(12) United States Patent
Shimamura et al.

(10) Patent No.: US 10,517,926 B2
(45) Date of Patent: Dec. 31, 2019

(54) OLIGOPEPTIDE HAVING PROINFLAMMATORY CYTOKINE SECRETION-INHIBITING ACTIVITY

(71) Applicant: Osaka University, Osaka (JP)

(72) Inventors: Munehisa Shimamura, Osaka (JP);
Hironori Nakagami, Osaka (JP);
Hitomi Kurinami, Osaka (JP); Ryuichi Morishita, Osaka (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 15/575,211

(22) PCT Filed: May 16, 2016

(86) PCT No.: PCT/JP2016/064446
§ 371 (c)(1),
(2) Date: Nov. 17, 2017

(87) PCT Pub. No.: WO2016/186071
PCT Pub. Date: Nov. 24, 2016

(65) Prior Publication Data
US 2018/0147259 A1 May 31, 2018

(30) Foreign Application Priority Data
May 20, 2015 (JP) .................. 2015-102502

(51) Int. Cl.
| | |
|---|---|
| A61K 38/17 | (2006.01) |
| C07K 7/06 | (2006.01) |
| A61P 29/00 | (2006.01) |
| A61P 19/10 | (2006.01) |
| A61P 35/00 | (2006.01) |
| A61K 38/19 | (2006.01) |
| C07K 14/47 | (2006.01) |
| C07K 14/52 | (2006.01) |

(52) U.S. Cl.
CPC .......... *A61K 38/1709* (2013.01); *A61K 38/19* (2013.01); *A61P 19/10* (2018.01); *A61P 29/00* (2018.01); *A61P 35/00* (2018.01); *C07K 7/06* (2013.01); *C07K 14/4703* (2013.01); *C07K 14/52* (2013.01)

(58) Field of Classification Search
None
See application file for complete search history.

(56) References Cited

U.S. PATENT DOCUMENTS

| | | | | |
|---|---|---|---|---|
| 5,288,931 | A * | 2/1994 | Chang .................. | C07K 1/1133 435/69.1 |
| 7,112,660 | B1 * | 9/2006 | Domingues ........ | C07K 14/5406 424/85.2 |
| 2003/0045474 | A1 * | 3/2003 | Sailer ................ | A61K 38/1875 514/8.8 |
| 2014/0051637 | A1 | 2/2014 | Suzumura et al. | |

FOREIGN PATENT DOCUMENTS

| | | |
|---|---|---|
| JP | 2003-505503 | 2/2003 |
| JP | 2005-514919 | 5/2005 |
| JP | 2011-213654 A | 10/2011 |
| WO | WO 01/08677 | 2/2001 |
| WO | WO 03/033664 | 4/2003 |
| WO | WO-2003/033663 A2 | 4/2003 |
| WO | WO-2009/003889 A2 | 1/2009 |
| WO | WO 2012/147805 | 11/2012 |
| WO | WO 2014/119438 | 8/2014 |
| WO | WO-2014/119438 | 8/2014 |

OTHER PUBLICATIONS

Tokuriki et al., 2009, Curr. Opin. Struc. Biol. 19:596-604).*
Bhattacharya et al. (2017, PLoS ONE 12(3): e0171355, https://doi.org/10.1371/journal.pone.0171355).*
Alaoui-Ismaili (2009, Cytokine Growth Factor Rev. 20(5-6):501-7).*
Guo et al. (2004, PNAS USA 101(25):9205-10).*
Ulloa-Aguirre et al. (2004, Traffic 5:821-837).*
Bernier et al. (2004, Curr. Opin. Pharmacol. 4:528-533).*
Yasuda, 2011. Translation of JP-20011213654, pp. 1-44.*
Bertrand, et al., "Transport characteristics of a novel peptide platform for CNS therapeutics," J. Cell. Mol. Med. vol. 14, No. 12, 2010, pp. 2827-2839.
Cheng, et al., "Mutations within the TNF-Like Core Domain of RANKL Impair Osteoclast Differentiation and Activation," Molecular Endocrinol, 2009, 23(1):35-46.
Kurinami, et al., "Session Title: Experimental Mechanisms and Models Oral Abstracts II," Stroke, 2016, vol. 47, Suppl. 1, A174.
Lam, et al., "Crystal structure of the TRANCE/RANKL cytokine reveals determinants of receptor-ligand specificity," The Journal of Clinical Investigation, 2001, vol. 108, No. 7, pp. 971-979.
Maruyama, et al., "Receptor Activator of NF-κB Ligand and Osteoprotegerin Regulate Proinflammatory Cytokine Production in Mice," The Journal of Immunology 2006; 177: 3799-3805.
Naidu, et al., "RANKL targeted peptides inhibit osteoclastogenesis and attenuate adjuvant induced arthritis by inhibiting NF-κB activation and down regulating inflammatory cytokines," Chemico-Biological Interactions 203 (2013) 467-479.
Utrera-Barillas, et al., "An anti-inflammatory oliopeptide produced by *Entamoeba histolytica* down-regulates the expression of proinflammatory chemokines," Parasite Immunology, 2003, 25, 475-482.

(Continued)

*Primary Examiner* — Elizabeth C. Kemmerer
(74) *Attorney, Agent, or Firm* — Cesari and McKenna LLP

(57) ABSTRACT

Provided is an oligopeptide having preventive and therapeutic effects on infarction diseases. The oligopeptide contains a DE loop sequence of RANKL protein, and has inhibitory activity on proinflammatory cytokine secretion from cells.

8 Claims, 13 Drawing Sheets

Specification includes a Sequence Listing.

(56) References Cited

OTHER PUBLICATIONS

Yao, et al., "Protective effects of MLIF analogs on cerebral ischemia-reperfusion injury in rats," Peptides, 32 (2011) 1047-1054.
Kurinami, et al., "RANK Signal o Target ni shita Nokosoku ni Okeru Shinki Chiryoho ni Tsuite no Kento", Anti-aging Science (2015), vol. 7, No. 3, p. 53 (189).
Xu et al, "Cloning, Sequencing, and Functional Characterization of the Rat Homologue of Receptor Activator of NF-κB Ligand". Journal of Bone and Mineral Research (2000) 15 (11): 2178-2186.
Examination Report dated Aug. 30, 2018 issued in corresponding Australian Patent Application No. 2016265523.
Hai Minh Ta et al; "Structure-based development of a receptor activator of nuclear factor-kB ligand (RANKL) inhibitor peptide and molecular basis for osteopetrosis"; Proceedings of the National Academy of Sciences of the United States of America, Nov. 23, 2010, vol. 107, No. 47, pp. 20281-20286.
Extended European Search Report dated May 20, 2019 in corresponding European Application No. 16 796 464.2.

\* cited by examiner

① no treat
② control si
③ siRNA against RANK

NFATc1: master gene for osteoclast differentiation
ACP5: osteoclast-specific marker
p65: nuclear phosphorylated p65

Two way ANOVA
Sidak's multiple comparisons test

```
SEQUENCE LISTING

<160> NUMBER OF SEQ ID NOS: 24

<210> SEQ ID NO 1
<211> LENGTH: 7
<212> TYPE: PRT
<213> ORGANISM: Homo sapiens

<400> SEQUENCE: 1

Ser Ile Lys Ile Pro Ser Ser
1               5

<210> SEQ ID NO 2
<211> LENGTH: 8
<212> TYPE: PRT
<213> ORGANISM: Mus musculus

<400> SEQUENCE: 2

Leu Met Val Tyr Val Val Lys Thr
1               5

<210> SEQ ID NO 3
<211> LENGTH: 11
<212> TYPE: PRT
<213> ORGANISM: Mus musculus

<400> SEQUENCE: 3

Tyr Leu Gln Leu Met Val Tyr Val Val Lys Thr
1               5                   10

<210> SEQ ID NO 4
<211> LENGTH: 8
<212> TYPE: PRT
<213> ORGANISM: Homo sapiens

<400> SEQUENCE: 4

Leu Met Val Tyr Val Thr Lys Thr
1               5

<210> SEQ ID NO 5
<211> LENGTH: 11
<212> TYPE: PRT
<213> ORGANISM: Homo sapiens

<400> SEQUENCE: 5

Tyr Leu Gln Leu Met Val Tyr Val Thr Lys Thr
1               5                   10

<210> SEQ ID NO 6
```

-continued

```
<211> LENGTH: 9
<212> TYPE: PRT
<213> ORGANISM: Mus musculus

<400> SEQUENCE: 6

His Asn Leu Met Lys Gly Gly Ser Thr
1               5

<210> SEQ ID NO 7
<211> LENGTH: 7
<212> TYPE: PRT
<213> ORGANISM: Mus musculus

<400> SEQUENCE: 7

His Asn Leu Met Lys Gly Gly
1               5

<210> SEQ ID NO 8
<211> LENGTH: 9
<212> TYPE: PRT
<213> ORGANISM: Homo sapiens

<400> SEQUENCE: 8

His Thr Leu Met Lys Gly Gly Ser Thr
1               5

<210> SEQ ID NO 9
<211> LENGTH: 7
<212> TYPE: PRT
<213> ORGANISM: Homo sapiens

<400> SEQUENCE: 9

His Thr Leu Met Lys Gly Gly
1               5

<210> SEQ ID NO 10
<211> LENGTH: 30
<212> TYPE: PRT
<213> ORGANISM: Mus musculus

<400> SEQUENCE: 10

Leu Met Val Tyr Val Val Lys Thr Ser Ile Lys Ile Pro Ser Ser His
1               5                   10                  15

Asn Leu Met Lys Gly Gly Ser Thr Lys Asn Trp Ser Gly Asn
            20                  25                  30

<210> SEQ ID NO 11
<211> LENGTH: 30
<212> TYPE: PRT
<213> ORGANISM: Mus musculus

<400> SEQUENCE: 11

Asp Tyr Leu Gln Leu Met Val Tyr Val Val Lys Thr Ser Ile Lys Ile
1               5                   10                  15

Pro Ser Ser His Asn Leu Met Lys Gly Gly Ser Thr Lys Asn
            20                  25                  30

<210> SEQ ID NO 12
<211> LENGTH: 15
<212> TYPE: PRT
<213> ORGANISM: Mus musculus

<400> SEQUENCE: 12

Leu Met Val Tyr Val Val Lys Thr Ser Ile Lys Ile Pro Ser Ser
```

```
<210> SEQ ID NO 13
<211> LENGTH: 22
<212> TYPE: PRT
<213> ORGANISM: Mus musculus

<400> SEQUENCE: 13

Leu Met Val Tyr Val Val Lys Thr Ser Ile Lys Ile Pro Ser Ser His
1               5                   10                  15

Asn Leu Met Lys Gly Gly
            20

<210> SEQ ID NO 14
<211> LENGTH: 30
<212> TYPE: PRT
<213> ORGANISM: Homo sapiens

<400> SEQUENCE: 14

Leu Met Val Tyr Val Thr Lys Thr Ser Ile Lys Ile Pro Ser Ser His
1               5                   10                  15

Thr Leu Met Lys Gly Gly Ser Thr Lys Tyr Trp Ser Gly Asn
            20                  25                  30

<210> SEQ ID NO 15
<211> LENGTH: 10
<212> TYPE: PRT
<213> ORGANISM: Mus musculus

<400> SEQUENCE: 15

His Glu Thr Ser Gly Ser Val Pro Ala Asp
1               5                   10

<210> SEQ ID NO 16
<211> LENGTH: 10
<212> TYPE: PRT
<213> ORGANISM: Homo sapiens

<400> SEQUENCE: 16

His Glu Thr Ser Gly Asp Leu Ala Thr Glu
1               5                   10

<210> SEQ ID NO 17
<211> LENGTH: 23
<212> TYPE: DNA
<213> ORGANISM: Artificial Sequence
<220> FEATURE:
<223> OTHER INFORMATION: RANK siRNA sequence

<400> SEQUENCE: 17
gcgcagacuu cacuccauau utt                                           23

<210> SEQ ID NO 18
<211> LENGTH: 23
<212> TYPE: DNA
<213> ORGANISM: Artificial Sequence
<220> FEATURE:
<223> OTHER INFORMATION: RANK siRNA sequence

<400> SEQUENCE: 18
uauggaguga agucugcgcu utt                                           23

<210> SEQ ID NO 19
<211> LENGTH: 23
```

```
<212> TYPE: DNA
<213> ORGANISM: Artificial Sequence
<220> FEATURE:
<223> OTHER INFORMATION: control siRNA sequence

<400> SEQUENCE: 19
uagcgacuaa acacaucaau utt                                              23

<210> SEQ ID NO 20
<211> LENGTH: 23
<212> TYPE: DNA
<213> ORGANISM: Artificial Sequence
<220> FEATURE:
<223> OTHER INFORMATION: control siRNA sequence

<400> SEQUENCE: 20
uuaucgcuga uuuguguagu utt                                              23

<210> SEQ ID NO 21
<211> LENGTH: 28
<212> TYPE: PRT
<213> ORGANISM: Mus musculus

<400> SEQUENCE: 21

His Glu Thr Ser Gly Ser Val Pro Ala Asp Tyr Leu Gln Leu Met Val
1               5                   10                  15

Tyr Val Val Lys Thr Ser Ile Lys Ile Pro Ser Ser
            20                  25

<210> SEQ ID NO 22
<211> LENGTH: 23
<212> TYPE: PRT
<213> ORGANISM: Mus musculus

<400> SEQUENCE: 22

Leu Met Val Tyr Val Val Lys Thr Ser Ile Lys Ile Pro Ser Ser His
1               5                   10                  15

Asn Leu Met Lys Gly Gly Ser
            20

<210> SEQ ID NO 23
<211> LENGTH: 26
<212> TYPE: PRT
<213> ORGANISM: Mus musculus

<400> SEQUENCE: 23

Leu Met Val Tyr Val Val Lys Thr Ser Ile Lys Ile Pro Ser Ser His
1               5                   10                  15

Asn Leu Met Lys Gly Gly Ser Thr Lys Asn
            20                  25

<210> SEQ ID NO 24
<211> LENGTH: 11
<212> TYPE: PRT
<213> ORGANISM: Mus musculus

<400> SEQUENCE: 24

Leu Met Val Tyr Val Val Lys Thr Ser Ile Lys
1               5                   10
```

OLIGOPEPTIDE HAVING PROINFLAMMATORY CYTOKINE SECRETION-INHIBITING ACTIVITY

CROSS REFERENCE TO RELATED APPLICATIONS

This application is the National Stage of International Application No. PCT/JP2016/064446, filed on May 16, 2016, which claims the benefit of Japanese Application No. 2015-102,502, filed on May 20, 2015. The contents of both applications are hereby incorporated by reference in their entirety.

TECHNICAL FIELD

The present invention relates to an oligopeptide having proinflammatory cytokine secretion-inhibiting activity, and a pharmaceutical preparation for preventing or treating infarction diseases, the pharmaceutical preparation comprising the oligopeptide.

BACKGROUND ART

Infarction diseases, such as cerebral infarction and cardiac infarction, are caused by the formation of ischemic areas due to vascular occlusion or the like. In general, due to the formation of ischemic areas, oxygen and nutrients are not supplied to their surrounding areas. Further, simultaneously with or following this, inflammatory reactions and free radical formation occur to thereby expand necrotic areas for a short period of time. It is therefore very important, in the treatment of infarction diseases, to administer effective therapeutic agents in a relatively early stage after the development of ischemic areas.

Examples of known cerebral infarction therapeutic agents with internationally approved efficiency include thrombolytic agents (tissue plasminogen activators). However, thrombolytic agents must be administered within 4.5 hours after the formation of ischemic areas; thus, they cannot be used for patients for whom the time of formation of ischemic areas is completely unknown, or patients for whom 4.5 hours or more has already elapsed after the formation of ischemic areas. Edaravone is also known as another cerebral infarction therapeutic agent; however, it is necessary to administer this agent several times (generally twice a day).

In contrast, the present inventors report that RANKL protein inhibits proinflammatory cytokines, and has preventive and therapeutic effects on infarction diseases (PTL 1). In this case, the full length of RANKL protein is used as an active ingredient; however, it is preferable to use a shorter oligopeptide as an active ingredient, in terms of stability, economical efficiency, etc. However, it was not known which region of RANKL protein inhibited proinflammatory cytokines in cells (particularly microglial cells, macrophage cells, etc.), and had preventive and therapeutic effects on infarction diseases.

CITATION LIST

Patent Literature

PTL 1: WO2014/051202
PTL 2: WO2012/147805

Non-Patent Literature

NPL 1: The Journal of Clinical Investigation, No. 7, Vol. 108, 2001, pages 971-979.
NPL 2: Mol Endocrinol, January 2009, 23 (1): 35-46.
NPL 3: J Cell Mol Med., 2010 December; 14 (12): 2827-2839.

SUMMARY OF INVENTION

Technical Problem

An object of the present invention is to provide an oligopeptide having preventive and therapeutic effects on infarction diseases, and a pharmaceutical preparation for preventing or treating infarction diseases, the pharmaceutical preparation comprising the oligopeptide. In particular, an object of the present invention is to provide a pharmaceutical preparation that can exhibit therapeutic effects on infarction diseases even when administered several hours (e.g., 4 hours) or more after the formation of ischemic areas.

Solution to Problem

As a result of extensive research, the present inventors found that the above object can be achieved by an oligopeptide containing a DE loop sequence of RANKL protein, and having inhibitory activity on proinflammatory cytokine secretion from cells. Further research was conducted based on this finding. Consequently, the present invention has been completed. Specifically, the present invention includes the following embodiments.

Item 1. An oligopeptide containing a DE loop sequence of RANKL protein, and having inhibitory activity on proinflammatory cytokine secretion from cells.

Item 2. The oligopeptide according to Item 1, wherein the DE loop sequence is the following amino acid sequence (a) or (b):

(a) the amino acid sequence represented by SEQ ID NO: 1, or (b) an amino acid sequence with substitution, deletion, addition, or insertion of one or more amino acids in the amino acid sequence represented by SEQ ID NO: 1.

Item 3. The oligopeptide according to Item 1 or 2, wherein the oligopeptide is free from a CD loop sequence of RANKL protein.

Item 4. The oligopeptide according to any one of Items 1 to 3, wherein the oligopeptide contains a β-strand D sequence of RANKL protein adjacent to the N-terminal side of the DE loop sequence.

Item 5. The oligopeptide according to Item 4, wherein the β-strand D sequence is the following amino acid sequence (c) or (d):

(c) the amino acid sequence represented by any one of SEQ ID NOs: 2 to 5, or (d) an amino acid sequence with substitution, deletion, addition, or insertion of one or more amino acids in the amino acid sequence represented by any one of SEQ ID NOs: 2 to 5.

Item 6. The oligopeptide according to any one of Items 1 to 5, wherein the oligopeptide contains a β-strand E sequence of RANKL protein adjacent to the C-terminal side of the DE loop sequence.

Item 7. The oligopeptide according to Item 6, wherein the β-strand E sequence is the following amino acid sequence (e) or (f):

(e) the amino acid sequence represented by any one of SEQ ID NOs: 6 to 9, or (f) an amino acid sequence with substitution, deletion, addition, or insertion of one or more amino acids in the amino acid sequence represented by any one of SEQ ID NOs: 6 to 9.

Item 8. The oligopeptide according to any one of Items 1 to 7, wherein the oligopeptide consists of the following amino acid sequence (g) or (h):

(g) the amino acid sequence represented by any one of SEQ ID NOs: 10 to 14 and 22 to 24, or (h) an amino acid sequence with substitution, deletion, addition, or insertion of one or more amino acids in the amino acid sequence represented by any one of SEQ ID NOs: 10 to 14 and 22 to 24.

Item 9. A pharmaceutical preparation comprising the oligopeptide according to any one of Items 1 to 8.

Item 10. The pharmaceutical preparation according to Item 9, wherein the pharmaceutical preparation is used to prevent or treat at least one disease selected from the group consisting of infarction diseases, osteoporosis, septicemia, bone lesions caused by multiple myeloma, bone lesions caused by solid cancer metastasis, and the like.

Advantageous Effects of Invention

The present invention can provide an oligopeptide having preventive and therapeutic effects on infarction diseases, and a pharmaceutical preparation for preventing or treating infarction diseases, the pharmaceutical preparation comprising the oligopeptide. This oligopeptide can exhibit therapeutic effects on infarction diseases even when administered 3 hours or more after the formation of ischemic areas, and thus can be applied to a larger number of patients.

Moreover, the use of this oligopeptide is expected to contribute to higher therapeutic effects on infarction diseases, compared with the administration of edaravone, which is a known therapeutic agent, or RANKL full-length protein, which reportedly has therapeutic effects on infarction diseases.

Furthermore, RANKL protein activates osteoclasts, whereas this oligopeptide does not have such a property; rather, the oligopeptide can inhibit the activation of osteoclasts by RANKL. Therefore, the use of this oligopeptide can suppress a decrease in bone density after the onset of infarction diseases, while treating the diseases.

In addition, the oligopeptide of the present invention can exhibit therapeutic effects on cerebral infarction even when administered by a route other than an intraventricular route (e.g., by an intravenous route).

Japan's national health expenditure for infarction diseases is very high (for example, the national health expenditure for cerebral infarction exceeded 1 trillion yen in 2009). The expenditure amount increases every year, along with the aging population. Moreover, as infarction diseases become more severe, the necessity for care after onset and the degree of care also increases. Therefore, the use of the oligopeptide of the present invention to allow infarction diseases to remain mild contributes to a reduction in health expenditures and nursing costs.

BRIEF DESCRIPTION OF DRAWINGS

In FIGS. 12A and 12B, the vertical axis represents the value obtained by dividing the mRNA expression levels of the measurement object by the GAPDH mRNA expression levels. In FIG. 12C, the vertical axis represents the absorbance (which indicates the amount of p65 in the nuclear protein, binding to DNA having the NFκB-binding sequence) measured by the TransAM NFκB p65 Kit.

DESCRIPTION OF EMBODIMENTS

1. Definition

Figure 1:
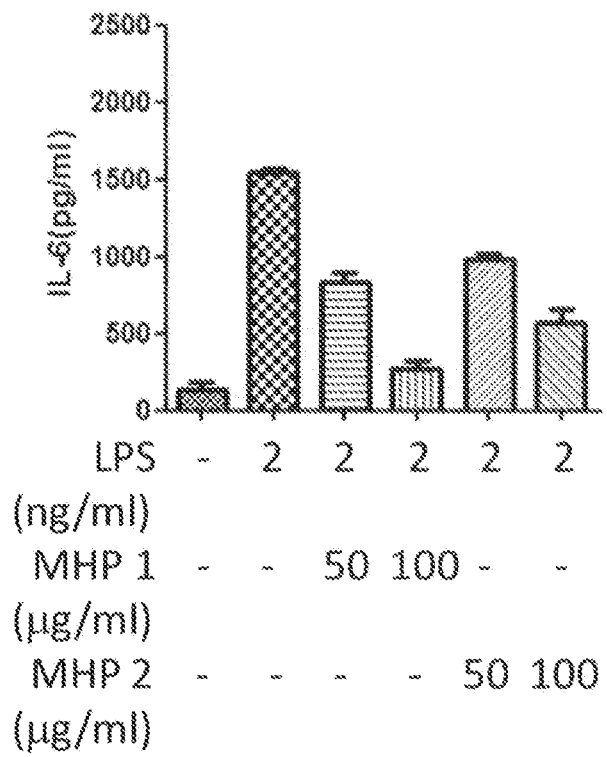
FIG. 1 shows the results of examining the influence of the RANKL peptide on the amount of proinflammatory cytokines (IL-6) secreted from microglial cells by lipopolysaccharide (LPS), which induces an inflammatory reaction (Example 2). The vertical axis represents the IL-6 concentration of the medium measured by ELISA. The numerical values of the horizontal axis represent the concentration of LPS, MHP1, or MHP2 in the medium, and "−" indicates that the concentration of LPS, MHP1, or MHP2 in the medium is 0.

In the present specification, the amino acid sequences are all represented by single letters.

In the present specification, the "identity" of amino acid sequences refers to the degree of identicalness of amino acid sequences in two or more comparable amino acid sequences. Therefore, as the identity of two amino acid sequences is higher, the identity or similarity of the sequences is higher. The level of amino acid sequence identity is determined, for example, by FASTA, which is a tool for sequence analysis, using default parameters. Alternatively, the level of amino acid sequence identity can be determined using the algorithm BLAST by Karlin and Altschul (Karlin S, Altschul SF, "Methods for assessing the statistical significance of molecular sequence features by using general scoring schemes," Proc. Natl Acad Sci USA. 87: 2264-2268 (1990); and Karlin S, Altschul SF, "Applications and statistics for multiple high-scoring segments in molecular sequences," Natl Acad Sci USA. 90: 5873-7 (1993)). A program called "BLASTX," which is based on this BLAST algorithm, has been developed. Specific procedures of these analysis methods are known, and reference may be made to the website (http://www.ncbi.nlm.nih.gov/) of the National Center of Biotechnology Information (NCBI).

In the present specification, the amino acid mutation in the oligopeptide is preferably a conservative substitution. Conservative substitution means that an amino acid residue is substituted with another amino acid residue having a similar side chain. For example, conservative substitution techniques include substitutions with amino acid residues having basic side chains, such as lysine, arginine, and histidine. Other examples of conservative substitutions include substitutions with the following amino acid resides: amino acid residues with acidic side chains, such as asparagic acid and glutamic acid; amino acid residues with uncharged polar side chains, such as glycine, asparagine, glutamine, serine, threonine, tyrosine, and cysteine; amino acid residues with nonpolar side chains, such as alanine, valine, leucine, isoleucine, proline, phenylalanine, methionine, and tryptophan; amino acid residues with β-branched side chains, such as threonine, valine, and isoleucine; and amino acid residues with aromatic side chains, such as tyrosine, phenylalanine, tryptophan, and histidine.

2. Oligopeptide

The present invention relates to an oligopeptide containing a DE loop sequence of RANKL protein, and having inhibitory activity on proinflammatory cytokine secretion from cells (this oligopeptide is also referred to as "the oligopeptide of the present invention" in the present specification). This is described below.

The DE loop sequence of RANKL protein is not particularly limited, as long as it is, among the amino acid sequences of RANKL protein, an amino acid sequence that forms a DE loop. The organism species from which the DE loop sequence is derived is not particularly limited. Examples include various mammals, such as humans, monkeys, mice, rats, dogs, cats, and rabbits. Among these, humans, monkeys, mice, rats, etc., are preferable; humans, mice, etc., are more preferable; and humans are even more preferable. DE loop sequences of various organism species are known. For example, those of mice and rats are disclosed in NPL 1, NPL 2, etc. Even if a DE loop sequence derived from a certain organism species is not known, the sequence can be easily determined based on known information (e.g., NPL 1 and NPL 2). Specific examples of the DE loop sequence of RANKL protein include the amino acid sequence represented by SEQ ID NO: 1 (a DE loop sequence of human- and mouse-derived RANKL protein), and the like.

The DE loop sequence of RANKL protein is preferably the following amino acid sequence (a) or (b):

(a) the amino acid sequence represented by SEQ ID NO: 1, or (b) an amino acid sequence with substitution, deletion, addition, or insertion of one or more amino acids (preferably one amino acid) in the amino acid sequence represented by SEQ ID NO: 1.

In (b) above, the number of "more amino acids" is, for example, 2 to 5, preferably 2 to 4, more preferably 2 or 3, and even more preferably 2.

Examples of the amino acid sequence (b) include (b') the amino acid sequence represented by N-terminus-serine (S)-isoleucine (I)-lysine (K)-C terminus. The inhibitory activity on proinflammatory cytokine secretion from cells can be determined, for example, in the following manner. When an oligopeptide targeted for activity measurement, together with a substance that induces an inflammatory reaction (e.g., lipopolysaccharide (LPS) or FSL-1), are brought into contact with microglial cells (e.g., MG6 cells) or macrophage cells (e.g., RAW264.7 cells and THP1 cells), if the amount of proinflammatory cytokines in the medium is less than that of control (without contact with the oligopeptide targeted for activity measurement), it can be determined that the oligopeptide targeted for activity measurement has inhibitory activity on proinflammatory cytokine secretion from cells. Specifically, the above determination can be performed according to the methods of Examples 2, 3, 9, 14, etc.

The oligopeptide of the present invention preferably does not contain a CD loop sequence of RANKL protein, in terms of more reliably (e.g., "in more cell strains," "for more inflammatory reactions through Toll-like receptors," and "more strongly") exhibiting the desired activity (inhibitory activity on proinflammatory cytokine secretion from cells).

The CD loop sequence of RANKL protein is not particularly limited, as long as it is, among the amino acid sequences of RANKL protein, an amino acid sequence that forms a CD loop. The organism species from which the CD loop sequence is derived is not particularly limited. Examples include various mammals, such as humans, monkeys, mice, rats, dogs, cats, and rabbits. Among these, humans, monkeys, mice, rats, etc., are preferable; humans, mice, etc., are more preferable; and humans are even more preferable. CD loop sequences of various organism species are known. For example, those of mice and rats are disclosed in NPL 1, NPL 2, etc. Even if a CD loop sequence derived from a certain organism species is not known, the sequence can be easily determined based on known information (e.g., NPL 1 and NPL 2). Specific examples of the CD loop sequence of RANKL protein include the amino acid sequence represented by SEQ ID NO: 15 (a CD loop sequence of mouse-derived RANKL protein), the amino acid sequence represented by SEQ ID NO: 16 (a CD loop sequence of human-derived RANKL protein), and the like.

The CD loop sequence of RANKL protein is preferably the following amino acid sequence (i) or (j):

(i) the amino acid sequence represented by SEQ ID NO: 15 or 16, or (j) an amino acid sequence with substitution, deletion, addition, or insertion of one or more amino acids (preferably one amino acid) in the amino acid sequence represented by SEQ ID NO: 15 or 16.

In (j) above, the number of "more amino acids" is, for example, 2 or 3, and preferably 2.

The oligopeptide of the present invention preferably contains a β-strand D sequence of RANKL protein adjacent to the N-terminal side of the above DE loop sequence, in terms of more reliably (e.g., "in more cell strains," "for more inflammatory reactions through Toll-like receptors," and "more strongly") exhibiting the desired activity (inhibitory activity on proinflammatory cytokine secretion from cells). The phrase "adjacent to the N-terminal side" indicates that the amino acid at the N-terminus of the above DE loop sequence and the amino acid at the C-terminus of the above β-strand D sequence are linked by a peptide bond.

The β-strand D sequence of RANKL protein is not particularly limited, as long as it is, among the amino acid sequences of RANKL protein, an amino acid sequence that forms β-strand D. The organism species from which the β-strand D sequence is derived is not particularly limited. Examples include various mammals, such as humans, monkeys, mice, rats, dogs, cats, and rabbits. Among these, humans, monkeys, mice, rats, etc., are preferable; humans, mice, etc., are more preferable; and humans are even more preferable. β-strand D sequences of various organism species are known. For example, those of mice and rats are disclosed in NPL 1, NPL 2, etc. Even if a β-strand D sequence derived from a certain organism species is not known, the sequence can be easily determined based on known information (e.g., NPL 1 and NPL 2). Specific examples of the β-strand D sequence of RANKL protein include the amino acid sequence represented by SEQ ID NO: 2 (part of a β-strand D sequence of mouse-derived RANKL protein), the amino acid sequence represented by SEQ ID NO: 3 (a β-strand D sequence of mouse-derived RANKL protein), the amino acid sequence represented by SEQ ID NO: 4 (part of a β-strand D sequence of human-derived RANKL protein), the amino acid sequence represented by SEQ ID NO: 5 (a β-strand D sequence of human-derived RANKL protein), and the like.

In SEQ ID NOs: 2 to 5, the leucine residue at the N-terminus of SEQ ID NOs: 2 and 4, and the leucine residue that is the fourth amino acid from the N-terminus of SEQ ID NOs: 3 and 5, are important for proinflammatory cytokine secretion-inhibiting activity. Therefore, when a β-strand D sequence is contained, it is preferable that these leucine residues be not mutated.

The β-strand D sequence of RANKL protein is preferably the following amino acid sequence (c) or (d):

(c) the amino acid sequence represented by any one of SEQ ID NOs: 2 to 5, or (d) an amino acid sequence with substitution, deletion, addition, or insertion of one or more amino acids (preferably one amino acid) in the amino acid sequence represented by any one of SEQ ID NOs: 2 to 5.

In (d) above, the number of "more amino acids" is, for example, 2 or 3, and preferably 2.

The oligopeptide of the present invention preferably contains a β-strand E sequence of RANKL protein adjacent to the C-terminal side of the above DE loop sequence, in terms of more reliably (e.g., "in more cell strains," "for more inflammatory reactions through Toll-like receptors," and "more strongly") exhibiting the desired activity (inhibitory activity on proinflammatory cytokine secretion from cells). The phrase "adjacent to the C-terminal side" indicates that the amino acid at the C-terminus of the above DE loop sequence and the amino acid at the N-terminus of the above β-strand E sequence are linked by a peptide bond.

The β-strand E sequence of RANKL protein is not particularly limited, as long as it is, among the amino acid sequences of RANKL protein, an amino acid sequence that forms β-strand E. The organism species from which the β-strand E sequence is derived is not particularly limited. Examples include various mammals, such as humans, monkeys, mice, rats, dogs, cats, and rabbits. Among these, humans, monkeys, mice, rats, etc., are preferable; humans, mice, etc., are more preferable; and humans are even more preferable. β-strand E sequences of various organism species are known. For example, those of mice and rats are disclosed in NPL 1, NPL 2, etc. Even if a β-strand E sequence derived from a certain organism species is not known, the sequence can be easily determined based on known information (e.g., NPL 1 and NPL 2). Specific examples of the β-strand E sequence of RANKL protein include the amino acid sequence represented by SEQ ID NO: 6 (a β-strand E sequence of mouse-derived RANKL protein), the amino acid sequence represented by SEQ ID NO: 7 (part of a β-strand E sequence of mouse-derived RANKL protein), the amino acid sequence represented by SEQ ID NO: 8 (a β-strand E sequence of human-derived RANKL protein), the amino acid sequence represented by SEQ ID NO: 9 (part of a β-strand E sequence of human-derived RANKL protein), and the like.

The β-strand E sequence of RANKL protein is preferably the following amino acid sequence (e) or (f):

(e) the amino acid sequence represented by any one of SEQ ID NOs: 6 to 9, or (f) an amino acid sequence with substitution, deletion, addition, or insertion of one or more amino acids (preferably one amino acid) in the amino acid sequence represented by any one of SEQ ID NOs: 6 to 9.

In (f) above, the number of "more amino acids" is, for example, 2 or 3, and preferably 2.

The length of the oligopeptide of the present invention is not particularly limited, as long as it is a general length as an oligopeptide. The length of the oligopeptide of the present invention is, for example, 5 to 50 amino acid residues, preferably 5 to 40 amino acid residues, and more preferably 6 to 35 amino acid residues.

The oligopeptide of the present invention may contain sequences other than the above-mentioned sequences, as long as it has inhibitory activity on proinflammatory cytokine secretion from cells. Other sequences are not particularly limited, but are preferably determined from the viewpoint, for example, that the entire oligopeptide is hydrophilic, or that the intracellular half-life is longer. The hydrophilicity of the oligopeptide and the intracellular half-life can be confirmed on various websites (e.g., ExPASy (http://web.expasy.org/protparam/)). When ExPASy is used, regarding hydrophilicity, it is preferable to design a sequence so that "grand average of hydropathicity" shows a negative value.

Moreover, when the oligopeptide of the present invention is used as an active ingredient of a pharmaceutical preparation for preventing or treating infarction diseases, sequences that are known to promote passage through the blood brain barrier may be added or inserted as other sequences, or low molecules that are known to promote passage through the blood brain barrier may be connected (e.g., PTL 2 and NPL 3).

In terms of more reliably (e.g., "in more cell strains," "for more inflammatory reactions through Toll-like receptors," and "more strongly") exhibiting the desired activity (inhibitory activity on proinflammatory cytokine secretion from cells), the oligopeptide of the present invention is preferably an oligopeptide consisting of the following amino acid sequence (g) or (h):

(g) the amino acid sequence represented by any one of SEQ ID NOs: 10 to 14 and 22 to 24, or (h) an amino acid sequence with substitution, deletion, addition, or insertion of one or more amino acids in the amino acid sequence represented by any one of SEQ ID NOs: 10 to 14 and 22 to 24.

In (h) above, the number of "more amino acids" is, for example, 2 to 5, preferably 2 or 3, and more preferably 2.

The oligopeptide of the present invention may be chemically modified, as long as it has inhibitory activity on proinflammatory cytokine secretion from cells.

The C-terminus of the oligopeptide of the present invention may be a carboxyl group (—COOH), carboxylate (—COO⁻), amide (—CONH$_2$), or ester (—COOR).

Examples of R in the ester include $C_{1-6}$ alkyl groups, such as methyl, ethyl, n-propyl, isopropyl, and n-butyl; $C_{3-8}$ cycloalkyl groups, such as cyclopentyl and cyclohexyl; $C_{6-12}$ aryl groups, such as phenyl and α-naphthyl; phenyl-$C_{1-2}$ alkyl groups, such as benzyl and phenethyl; $C_{7-14}$ aralkyl groups, such as α-naphthyl-$C_{1-2}$ alkyl groups (e.g., α-naphthylmethyl); pivaloyloxymethyl groups; and the like.

Furthermore, the oligopeptide of the present invention also includes those in which the amino group of the N-terminal amino acid residue is protected by a protecting group (e.g., $C_{1-6}$ acyl groups such as $C_{1-6}$ alkanoyl, including formyl and acetyl groups), etc.

The oligopeptide of the present invention includes those having various forms, such as linear oligopeptides, branched oligopeptides, and cyclic oligopeptides; however, linear oligopeptides are preferable. Moreover, the oligopeptide of the present invention may be crosslinked by or based on a known means, as long as it has inhibitory activity on proinflammatory cytokine secretion from cells.

The oligopeptide of the present invention may be in the form of a pharmaceutically acceptable salt with an acid or a base. The salt is not particularly limited, as long as it is a pharmaceutically acceptable salt. Acid salts and basic salts can both be employed. Examples of acid salts include inorganic acid salts, such as hydrochloride, hydrobromate, sulfate, nitrate, and phosphate; organic acid salts, such as acetate, propionate, tartrate, fumarate, maleate, malate, citrate, methanesulfonate, and p-toluenesulfonate; amino acid salts, such as aspartate and glutamate; and the like. Moreover, examples of basic salts include alkali metal salts, such as sodium salt and potassium salt; alkaline earth metal salts, such as calcium salt and magnesium salt; and the like.

The oligopeptide of the present invention may in the form of a solvate. The solvent is not particularly limited, as long as it is pharmaceutically acceptable. Examples include water, ethanol, glycerol, acetic acid, and the like.

The oligopeptide of the present invention can be produced by a known peptide synthesis method, depending on its amino acid sequence.

3. Pharmaceutical Preparation

The present invention relates to a pharmaceutical preparation comprising the oligopeptide of the present invention (this pharmaceutical preparation is also referred to as "the pharmaceutical preparation of the present invention" in the present specification). This is described below.

The pharmaceutical preparation of the present invention is useful for the prevention or treatment of, for example, infarction diseases, osteoporosis, septicemia, bone lesions caused by multiple myeloma, bone lesions caused by solid cancer metastasis, and the like.

In the present invention, infarction diseases refer to conditions in which, due to the formation of ischemic areas, necrotic areas of tissue around the ischemic areas are expanding or have expanded. Examples of the cause of the formation of ischemic areas include vascular occlusion caused by the clogging of blood vessels with thrombi, emboli, etc. Examples of the cause of vascular occlusion include the clogging of blood vessels with thrombi or emboli, the narrowing of blood vessels, and the like.

Specific examples of infarction diseases include cerebral infarction, cardiac infarction, pulmonary infarction, renal infarction, lower-extremity acute artery obstruction, cerebral infarction by vasospasm after subarachnoid hemorrhage, infarction in the spleen, infarction in the liver, infarction in the intestinal tract, infarction in the testis, infarction in the ovary, and the like; preferably cerebral infarction, cardiac infarction, pulmonary infarction, renal infarction, lower-extremity acute artery obstruction, cerebral infarction caused by vasospasm after subarachnoid hemorrhage, and infarction in the spleen; more preferably cerebral infarction and cardiac infarction; and even more preferably cerebral infarction.

In the present invention, the prevention or treatment of infarction diseases means that expansion of necrotic areas formed around ischemic areas is suppressed by administering the pharmaceutical preparation of the present invention before or after the formation of the ischemic areas.

In the present invention, osteoporosis refers to a condition with a reduced bone density. The osteoporosis to be prevented or treated by the pharmaceutical preparation of the present invention is preferably osteoporosis that develops in association with the onset of infarction disease.

The pharmaceutical preparation of the present invention may also be the oligopeptide of the present invention itself, or a composition containing components (hereinafter also referred to as "additives") other than the oligopeptide of the present invention. Additives are not particularly limited, as long as they are pharmaceutically acceptable components. Examples include bases, carriers, solvents, dispersants, emulsifiers, buffers, stabilizers, excipients, binders, disintegrators, lubricants, thickeners, moisturizers, coloring agents, perfumes, chelating agents, and the like. When the pharmaceutical preparation of the present invention contains additives, the pharmaceutical preparation of the present invention can be produced using the additives according to a known method, depending on the dosage form.

The pharmaceutical preparation of the present invention may be in any dosage form, such as tablets, pills, powders, liquid formulations, injections, suspensions, emulsions, powders, granules, or capsules; injections are preferable.

The administration target of the pharmaceutical preparation of the present invention is a patient with an infarction disease, osteoporosis, or septicemia, or a subject who may develop an infarction disease, osteoporosis, or septicemia. The patient with an infarction disease, osteoporosis, or septicemia refers to a patient who has developed an infarction disease, osteoporosis, or septicemia, described above. The subject who may develop an infarction disease, osteoporosis, or septicemia refers to a subject who has sign symptoms of infarction disease, osteoporosis, or septicemia, described above, and who is diagnosed with the possibility of developing an infarction disease, osteoporosis, or septicemia.

Examples of the administration route of the pharmaceutical preparation of the present invention include oral administration, parenteral administration, and the like. More specific examples of the administration route include subcutaneous administration, intravenous administration, arterial administration, intracutaneous administration, intramuscular administration, intraosseous administration, intracardiac administration, intraventricular administration, subarachnoid administration, and intraperitoneal administration. When the target to be prevented or treated is an infarction disease, the pharmaceutical preparation of the present invention may be administered to the organ in which the infarction disease is developed.

The content of the oligopeptide of the present invention in the pharmaceutical preparation of the present invention is not particularly limited, as long as therapeutic effects can be exhibited for infarction diseases, osteoporosis, or septicemia. For example, the content of the oligopeptide is 0.01 to 80 wt. %, and preferably 1 to 50 wt. %.

The dosage form and effective dose of the pharmaceutical preparation of the present invention are dependent on the administration target, administration route, dosage form, patient's condition, doctor's decision, etc., and are not limited. For example, 1 ng to 100 mg can be administered to an adult with a body weight of 60 kg per administration.

As the dosage form for use in the treatment of infarction diseases, it is preferable to administer the pharmaceutical preparation of the present invention several times, for example, every minute to every ten hours, after the formation of ischemic areas. The pharmaceutical preparation of the present invention is excellent in that even when the first administration is performed 3 hours or more after the formation of ischemic areas, the pharmaceutical preparation can exhibit therapeutic effects on infarction diseases. Therefore, when used for the treatment of infarction diseases, the pharmaceutical preparation of the present invention can be used such that the first administration is performed immediately after the formation of ischemic areas, or 1 hour or more, 3 hours or more, 4 hours or more, or 6 hours or more after the formation of ischemic areas. In this case, the upper limit of administration timing is not particularly limited; for example, it is 10 hours, preferably 8 hours, and more preferably 6 hours, after the formation of ischemic areas.

When used for the prevention or treatment of infarction diseases, the pharmaceutical preparation of the present invention may be used in combination with other preventive or therapeutic agents for infarction diseases. Examples of other preventive or therapeutic agents include alteplase, edaravone, heparin, low-molecular-weight heparin, sodium ozagrel, argatroban, aspirin, Pradaxa, warfarin, glycerol, mannitol, clopidogrel, cilostazol, and the like. Such other preventive or therapeutic agents may be used singly or in combination of two or more. Furthermore, when used for the prevention or treatment of other diseases, the pharmaceutical preparation of the present invention may be used in combination with suitable pharmaceutical preparations.

EXAMPLES

The present invention is described in detail below based on Examples; however, the present invention is not limited to these Examples.

Example 1: Synthesis of Oligopeptides

Synthesis of oligopeptides consisting of amino acid sequences shown in Table 1 was entrusted to ILS Inc. It was confirmed by HPLC and MS that oligopeptides with the desired sequences were synthesized with high purity. Hereinafter, these peptides are also generically referred to as "the RANKL peptide." The amino acid sequence of MHP1 is represented by SEQ ID NO: 10, the amino acid sequence of MHP2 is represented by SEQ ID NO: 11, the amino acid sequence of MHP4 is represented by SEQ ID NO: 12, the amino acid sequence of MHP5 is represented by SEQ ID NO: 13, the amino acid sequence of MHP6 is represented by SEQ ID NO: 14, the amino acid sequence of MHP3 is represented by SEQ ID NO: 21, the amino acid sequence of MHP12 is represented by SEQ ID NO: 22, the amino acid sequence of MHP13 is represented by SEQ ID NO: 23, and the amino acid sequence of MHP17 is represented by SEQ ID NO: 24.

TABLE 1

| Name | Sequence | Species origin | Number of amino acids |
|---|---|---|---|
| MHP1 | LMVYVVKTSIKIPSSHNLMKGGS TKNWSGN | Mouse | 30 |
| MHP2 | DYLQLMVYVVKTSIKIPSSHNLM KGGSTKN | Mouse | 30 |
| MHP3 | HETSGSVPADYLQLMVYVVKTSI KIPSS | Mouse | 28 |
| MHP4 | LMVYVVKTSIKIPSS | Mouse | 15 |
| MHP5 | LMVYVVKTSIKIPSSHNLMKGG | Mouse | 22 |
| MHP6 | LMVYVTKTSIKIPSSHTLMKGGS TKYWSGN | Human | 30 |
| MHP12 | LMVYVVKTSIKIPSSHNLMKGGS | Mouse | 23 |
| MHP13 | LMVYVVKTSIKIPSSHNLMKGGS TKN | Mouse | 26 |
| MHP17 | LMVYVVKTSIK | Mouse | 11 |

Example 2: Proinflammatory Cytokine Secretion Inhibition by RANKL Peptide (Microglial Cells)

The influence of the RANKL peptide on the amount of proinflammatory cytokines secreted from microglial cells by lipopolysaccharide (LPS), which induces an inflammatory reaction, was examined. The specific examination procedures were as follows.

MG6 cells (mouse-derived microglial cell line) were cultured in a DMEM medium (+4% FBS) containing MHP1 or MHP2 (final concentration: 50 or 100 µg/ml), and LPS (final concentration: 2 ng/ml) for 24 hours by a standard method. After culture, the concentrations of IL-6 and TNFα in the medium were measured by the ELISA method. In the Examples of the present application, the ELISA method was performed using a kit (Quantikine ELISA Mouse TNF-α or Quantikine ELISA Mouse IL-6, produced by R&D Systems). The results are shown in FIG. 1 (IL-6) and FIG. 2 (TNFα).

Figure 2:
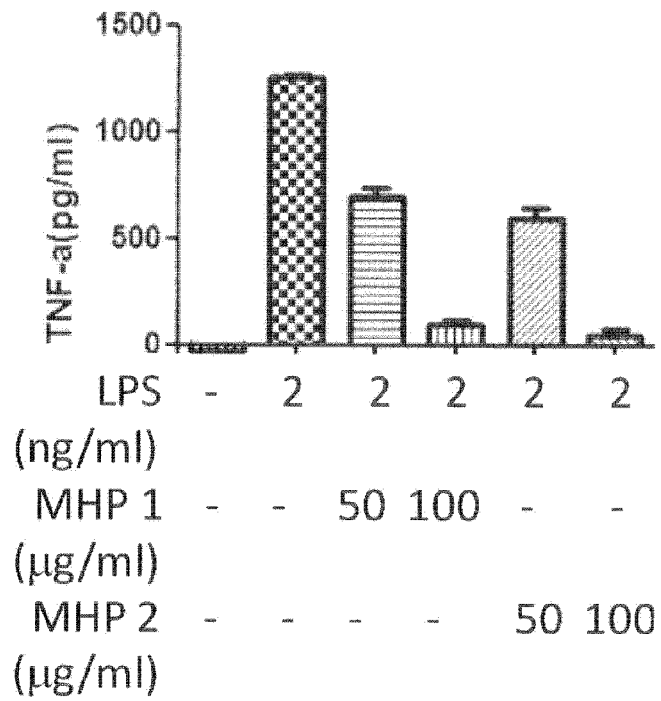
FIG. 2 shows the results of examining the influence of the RANKL peptide on the amount of proinflammatory cytokines (TNFα) secreted from microglial cells by lipopolysaccharide (LPS), which induces an inflammatory reaction (Example 2). The vertical axis represents the TNFα concentration of the medium measured by ELISA. The numerical values of the horizontal axis represent the concentration of LPS, MHP1, or MHP2 in the medium, and "−" indicates that the concentration of LPS, MHP1, or MHP2 in the medium is 0.

FIGS. 1 and 2 revealed that the increase in the amount of proinflammatory cytokine (IL-6 and TNFα) secretion by LPS (comparison between the first column and the second column from the left) was suppressed by MHP1 and MHP2 (comparison between the second column and the third to sixth columns from the left).

When the same test was also conducted on MHP3 to MHP5, MHP12, MHP13, and MHP17, MHP3 did not show proinflammatory cytokine secretion-inhibiting activity on the MG6 cells; however, MHP4, MHP5, MHP12, MHP13, and MHP17 showed proinflammatory cytokine secretion-inhibiting activity, in the same manner as MHP1 and MHP2.

Example 3: Proinflammatory Cytokine Secretion Inhibition by RANKL Peptide (Macrophage Cells)

The influence of the RANKL peptide on the amount of proinflammatory cytokines secreted from macrophage cells by LPS was examined. The specific examination procedures were as follows.

RAW264.7 cells (mouse-derived macrophage cell line) were cultured in a DMEM medium (+4% FBS) containing MHP1 (final concentration: 30, 50, or 100 µg/ml) and LPS (final concentration: 2 ng/ml) for 24 hours by a standard method. After culture, the concentrations of IL-6 and TNFα in the medium were measured by the ELISA method. The results are shown in FIG. 3 (IL-6) and FIG. 4 (TNFα).

Figure 3:
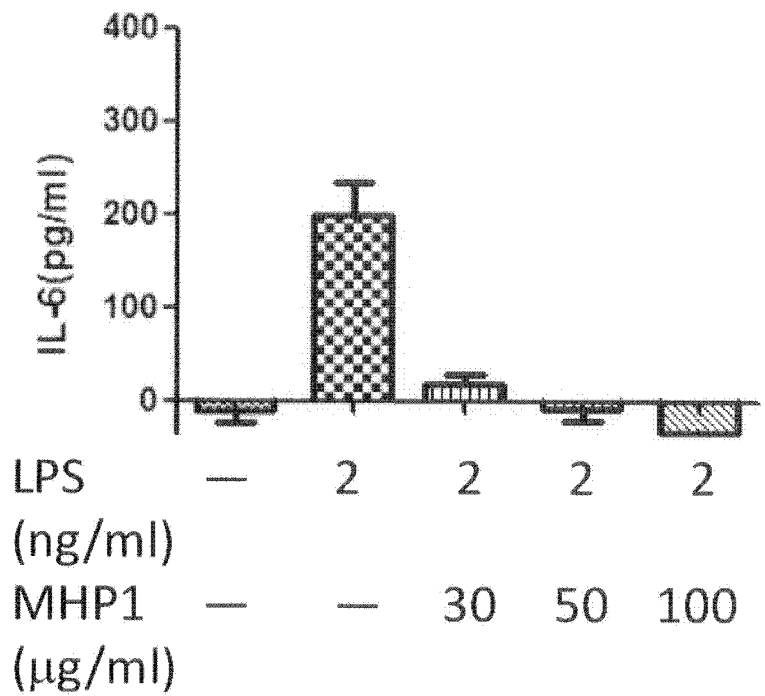
FIG. 3 shows the results of examining the influence of the RANKL peptide on the amount of proinflammatory cytokines (IL-6) secreted from macrophage cells by lipopolysaccharide (LPS), which induces an inflammatory reaction (Example 3). The vertical axis represents the IL-6 concentration of the medium measured by ELISA. The numerical values of the horizontal axis represent the concentration of LPS or MHP1 in the medium, and "−" indicates that the concentration of LPS or MHP1 in the medium is 0.
Figure 4:
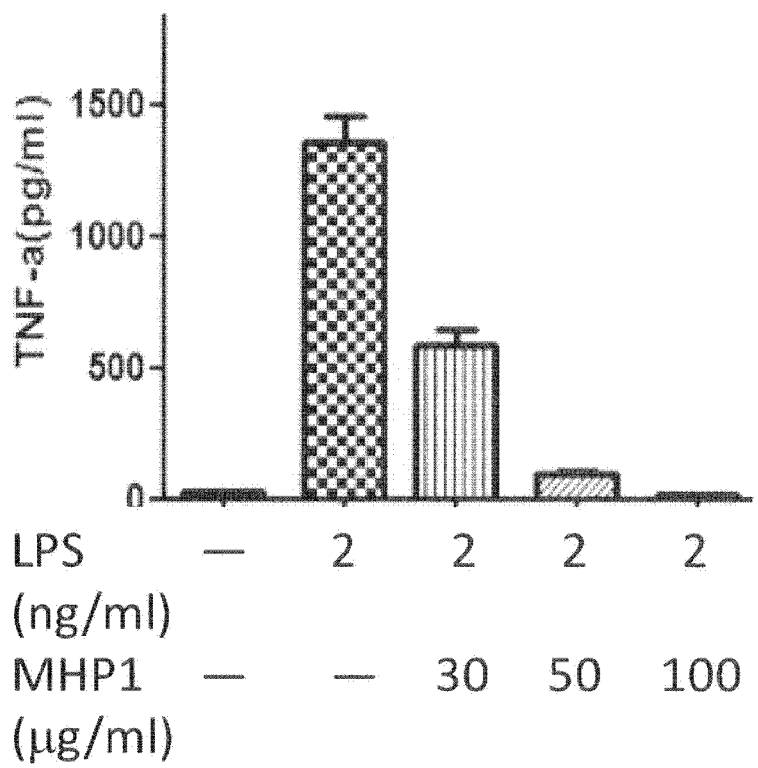
FIG. 4 shows the results of examining the influence of the RANKL peptide on the amount of proinflammatory cytokines (TNFα) secreted from macrophage cells by lipopolysaccharide (LPS), which induces an inflammatory reaction (Example 3). The vertical axis represents the TNFα concentration of the medium measured by ELISA. The numerical values of the horizontal axis represent the concentration of LPS or MHP1 in the medium, and "−" indicates that the concentration of LPS or MHP1 in the medium is 0.

FIGS. 3 and 4 revealed that the increase in the amount of proinflammatory cytokine (IL-6 and TNFα) secretion by LPS (comparison between the first column and the second column from the left) was suppressed by MHP1 (comparison between the second column and the third to fifth columns from the left).

Example 4: Neuroprotective Effect of RANKL Peptide (Neuron-Glia Mixed Culture System)

The influence of the RANKL peptide on neurons by LPS was examined in a neuron-glia mixed culture system. The specific examination procedures were as follows.

Neuronal tissue (a mixture of neurons and glial cells) was removed from a mouse fetus 21 days after fertilization (21st fetal day), and cultured in Neurobasal medium (+B-27, +5% HS) for 9 days. Then, the cells were divided into 3 groups (A to C groups), and subjected to the following treatments.

A Group

Figure 5:
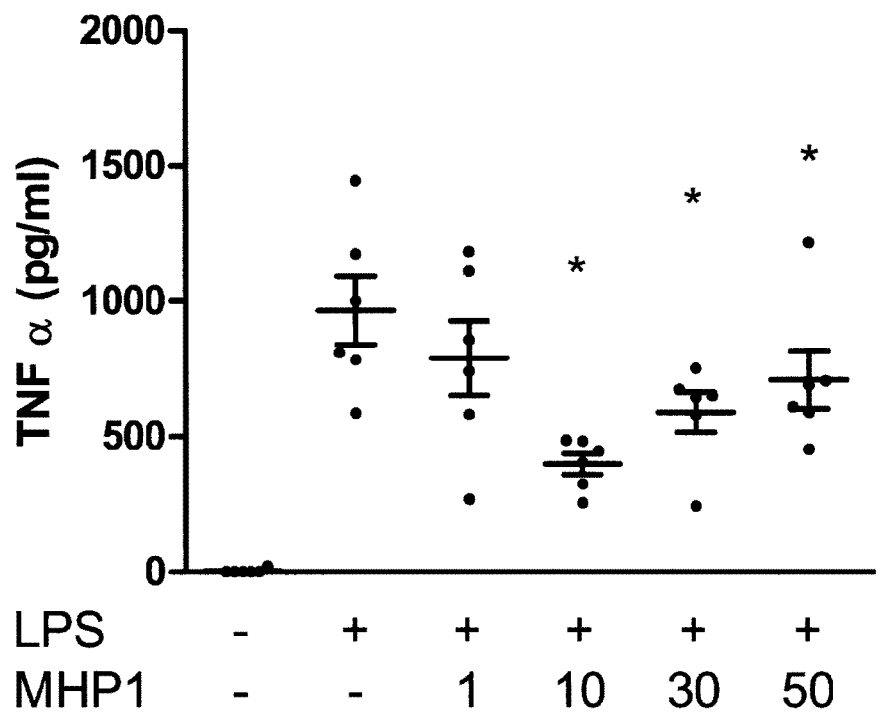
FIG. 5 shows the results of examining the influence of the RANKL peptide (pretreatment) on the amount of proinflammatory cytokines (TNFα) secreted by LPS in a neuron-glia mixed culture system (A group of Example 4). The vertical axis represents the TNFα concentration of the medium measured by ELISA. The numerical values of the horizontal axis represent the concentration (μg/ml) of MHP1 in the medium, "−" indicates that the concentration of LPS or MHP1 in the medium is 0, and "+" indicates that the concentration of LPS in the medium is 10 μg/ml. "*" indicates that the P-value relative to the case of LPS+ and MHP1− (the second column from the left) was less than 0.05.

The cells were cultured for 24 hours after the medium was changed to a medium (Neurobasal A/N2 supplement) containing MHP1 (final concentration: 1, 10, 30, or 50 µg/ml). Then, LPS (final concentration: 10 µg/ml) was added to the medium, and the cells were further cultured for 24 hours. After culture, the concentration of TNFα in the medium was measured by the ELISA method. FIG. 5 shows the results.

B Group

Figure 6:
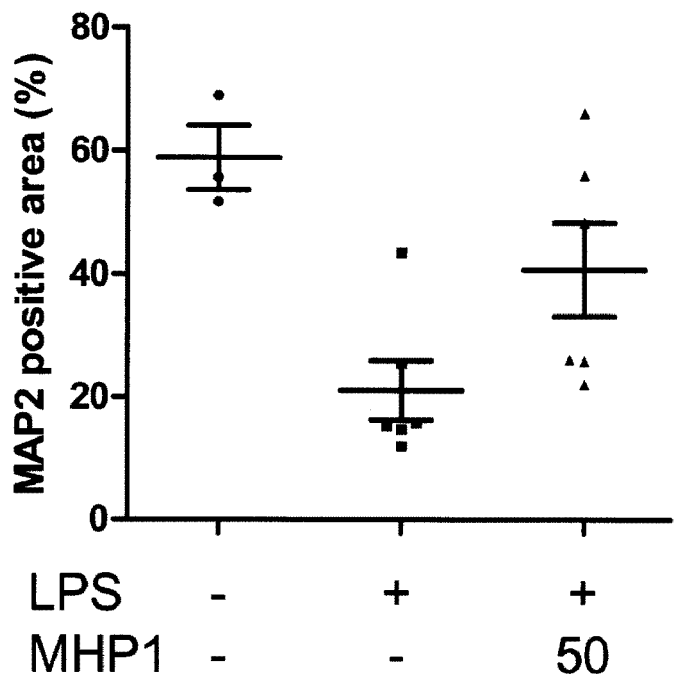
FIG. 6 shows the results of examining the influence of the RANKL peptide (pretreatment) on neuronal cell death by LPS in a neuron-glia mixed culture system (B group of Example 4). The vertical axis represents the ratio of the area of regions stained with an antibody against a neuronal marker (MAP2) (that is, regions occupied by survival neurons) relative to the culture dish area. The numerical value of the horizontal axis represents the concentration (μg/ml) of MHP1 in the medium, "−" indicates that the concentration of LPS or MHP1 in the medium is 0, and "+" indicates that the concentration of LPS in the medium is 10 μg/ml.

The cells were cultured for 24 hours after the medium was changed to a medium (Neurobasal A/N2 supplement) containing MHP1 (final concentration: 50 µg/ml). Then, LPS (final concentration: 10 µg/ml) was added to the medium, and the cells were further cultured for 5 days. After culture, immunostaining was performed according to a general method using an antibody (M4403, produced by Sigma-Aldrich) against MAP2, which was a neuronal cell marker, as a primary antibody (primary antibody: 1/1000 dilution, and second antibody (A 11001, produced by Invitrogen): 1/1000 dilution). The staining images were observed, and the ratio of the area of the stained region (i.e., the region occupied by the survival neurons) to the culture dish area was calculated. FIG. 6 shows the results.

C Group

Figure 7:
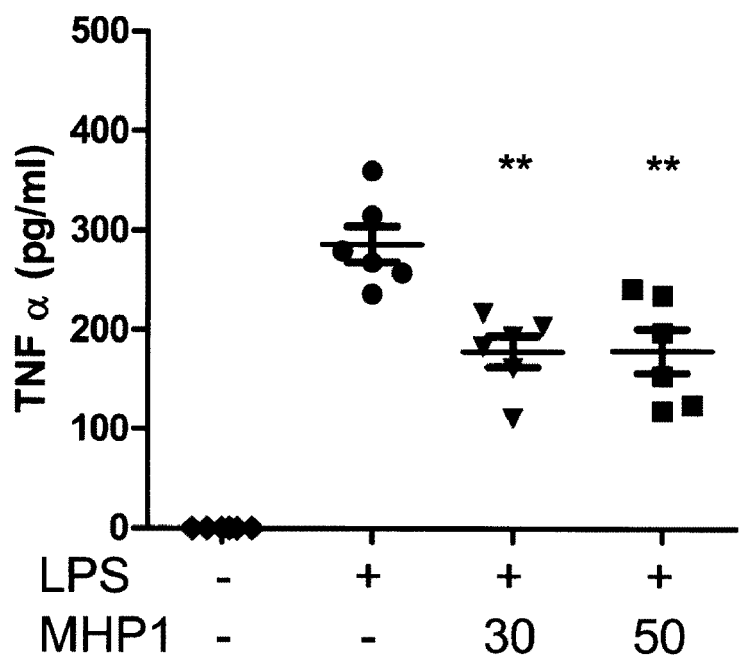
FIG. 7 shows the results of examining the influence of the RANKL peptide (simultaneous treatment) on the amount of proinflammatory cytokines (TNFα) secreted by LPS in a neuron-glia mixed culture system (C group of Example 4). The vertical axis represents the TNFα concentration of the medium measured by ELISA. The numerical values of the horizontal axis represent the concentration (μg/ml) of MHP1 in the medium, "−" indicates that the concentration of LPS or MHP1 in the medium is 0, and "+" indicates that the concentration of LPS in the medium is 10 μg/ml. "**" indicates that the P-value relative to the case of LPS+ and MHP1− (the second column from the left) was less than 0.01.

The cells were cultured for 24 hours after the medium was changed to a medium (Neurobasal A/N2 supplement) containing MHP1 (final concentration: 30 or 50 µg/ml) and LPS (final concentration: 10 µg/ml). After culture, the concentration of TNFα in the medium was measured by the ELISA method. FIG. 7 shows the results.

FIGS. 5 and 7 revealed that either when MHP1 was added before the addition of LPS (pretreatment) (A group), or when MHP1 was added simultaneously with the addition of LPS (simultaneous treatment) (C group), the increase in the amount of proinflammatory cytokine (TNFα) secretion by LPS (comparison between the first bar and the second bar from the left) was suppressed by MHP1 (comparison between the second bar from the left and the bars on the right side of the second bar). Further, FIG. 6 revealed that neuronal cell death by LPS (comparison between the first bar and the second bar from the left) was suppressed by MHP1 (comparison between the second bar and the third bar from the left).

Example 5: M1 Shift Suppression by RANKL Peptide

Microglial cells are present in two states: neuron-damaging M1 that produces proinflammatory cytokines etc., and neuron-protecting M2 that produces anti-inflammatory cytokines etc. It is known that the state of microglial cells is shifted to M1 (neuron-damaging) by LPS stimulus. The influence of the RANKL peptide on the M1 shift was examined. The specific examination procedures were as follows.

Figure 8:
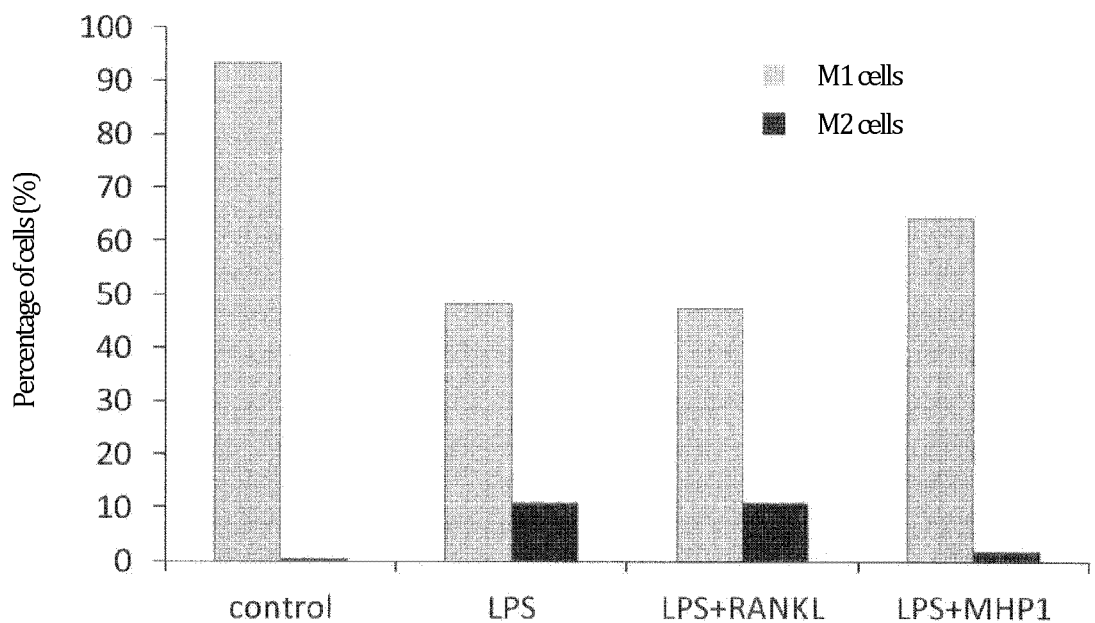
FIG. 8 shows the results of examining the influence of the RANKL peptide on the M1 shift by LPS (Example 5). The vertical axis represents the percentage of microglial cells in M1 or M2 state. In the horizontal axis, "control" represents a case in which any of LPS, RANKL protein, and RANKL peptide was contained in the medium, "LPS" represents a case in which only LPS was contained in the medium, "LPS+RANKL" represents a case in which LPS and RANKL protein were contained in the medium, and "LPS+ MHP1" represents a case in which LPS and RANKL peptide (MHP1) were contained in the medium.

MG6 cells (mouse-derived microglial cell line) were cultured in a DMEM medium (+4% FBS) containing MHP1 (final concentration: 100 µg/ml) or RANKL protein (Recombinant Murin sRANKL Ligand (Cat No. 315-11): produced by Peprotech) (final concentration: 10 ng/ml), and LPS (final concentration: 2 ng/ml) for 24 hours by a standard method. After culture, the cells were washed with PBS, and Fc receptor blocking was performed using mouse IgG. Thereafter, F4/80-FITC (microglia marker antibody) and CD206-APC (M2 marker antibody) were added, and reacted at 4° C. for 30 minutes in a dark place. After the reaction, the cells were washed with PBS, and the percentage of microglia marker-positive and M2 marker-positive (M2 state) cells, and the percentage of microglia marker-positive and M2 marker-negative (M1 state) cells were measured by FACS analysis (FACSCanto II, produced by BD Biosciences). FIG. 8 shows the results.

FIG. 8 revealed that the M1 shift caused by LPS (comparison between the first column and the second column from the left) was suppressed by MHP1 (comparison between the second column and the fourth column from the left).

Example 6: RANK Dependency of Anti-Inflammatory Activity of RANKL Peptide

An examination was conducted into whether proinflammatory cytokine secretion inhibition by the RANKL peptide (Example 2, etc.) occurred in the absence of RANK. The specific examination procedures were as follows.

Figure 9:
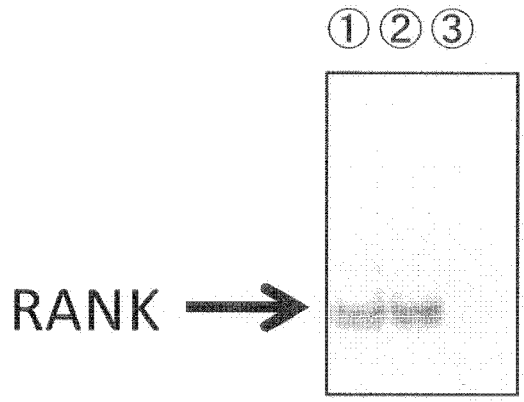
FIG. 9 shows that RANK of RAW264.7 cells was knocked down (Example 6). The position indicated by the arrow is the position of the band of RANK.

RAW264.7 cells were suspended in a DMEM medium (+10% FBS), seeded on a 24-well plate, and cultured at 37° C. at a $CO_2$ concentration of 5%. To 100 µl of serum-free DMEM medium, 37.5 ng (final concentration: 5 nM) of siRNA against RANK (a double strand of the sequence represented by SEQ ID NO: 17 and the sequence represented by SEQ ID NO: 18, produced by GeneDesign) or 37.5 ng (final concentration: 5 nM) of control siRNA (a double strand of the sequence represented by SEQ ID NO: 19 and the sequence represented by SEQ ID NO: 20, produced by GeneDesign), and 3 µl of HiPerFect Transfection Reagent (QIAGEN) were added, and the resultant was allowed to stand at room temperature for 10 minutes. This was added to the RAW264.7 cell culture medium. After culture at 37° C. at a $CO^2$ concentration of 5% for 24 hours, the cells were collected. A protein extract was obtained from the cells by a standard method, and RANK in this extract was detected at a dilution concentration of 1/100 by the Western blotting method (anti-RANK antibody: anti-mRANK (Cat. No. AF692), produced by R&D Systems). FIG. 9 shows the results. FIG. 9 confirmed that RANK was knocked down by siRNA against RANK (comparison between lane 2 and lane 3).

Figure 10:
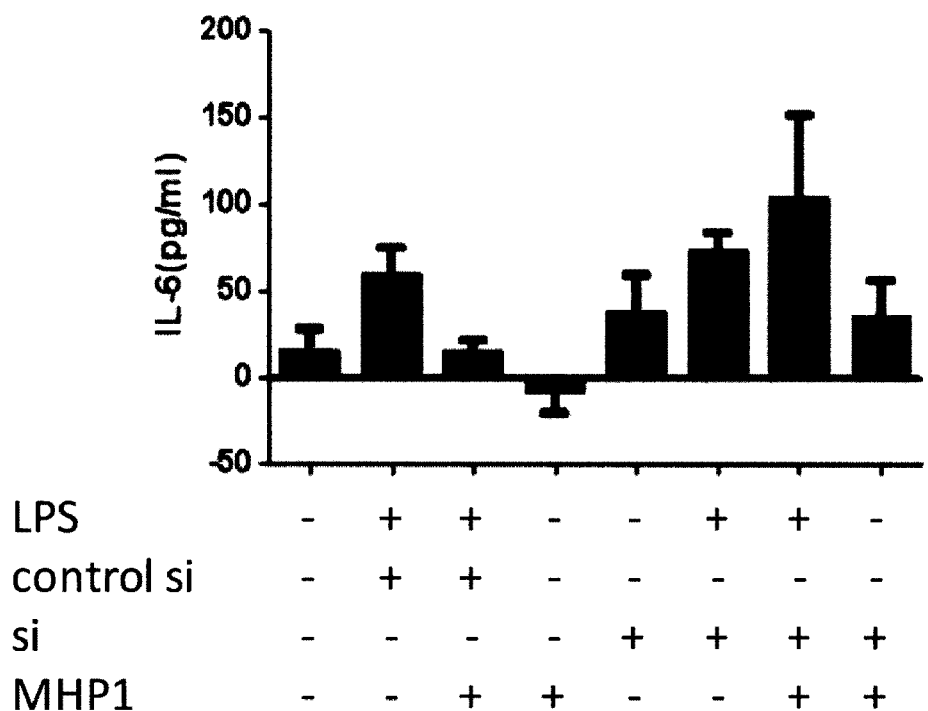
FIG. 10 shows the results of examining whether proinflammatory cytokine secretion inhibition by the RANKL peptide occurs in the absence of RANK (Example 6). The vertical axis represents the IL-6 concentration of the medium measured by ELISA. In the horizontal axis, "control si" represents control siRNA, "si" represents siRNA against RANK, and "+/−" represents the presence of the components shown on the left side.
Figure 11:
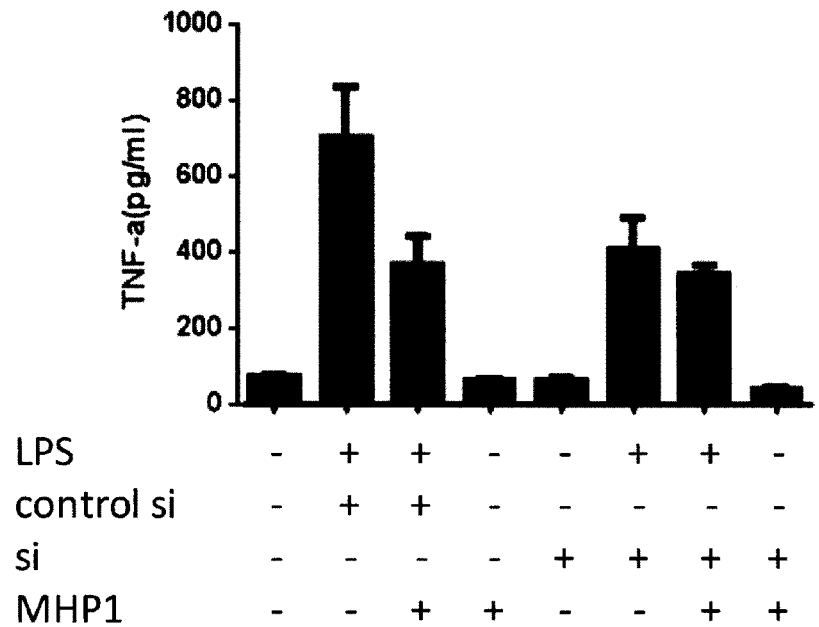
FIG. 11 shows the results of examining whether proinflammatory cytokine secretion inhibition by the RANKL peptide occurs in the absence of RANK (Example 6). The vertical axis represents the TNFα concentration of the medium measured by ELISA. In the horizontal axis, "control si" represents control siRNA, "si" represents siRNA against RANK, and "+/−" represents the presence of the components shown on the left side.

MHP1 and LPS were made to act on RANK knockdown cells, as in Example 3, and the concentrations of IL-6 and TNFα in the medium were measured by the ELISA method. FIGS. 10 and 11 show the results.

FIGS. 10 and 11 indicated that the secretion of proinflammatory cytokines (IL-6 and TNFα) was inhibited by MHP1 in the control siRNA-introduced cells (comparison between the second column and the third column from the left), whereas the secretion of the proinflammatory cytokines was not inhibited by MHP1 in the cells into which siRNA against RANK was introduced (RANK knockdown cells) (comparison between the sixth column and the seventh column from the left). This suggested that the anti-inflammatory activity of the RANKL peptide was dependent on RANK.

Example 7: Analysis 1 of Influence of RANKL Peptide on Osteoclasts

It has recently been reported that the administration of RANKL protein to mice induces the activation of osteoclasts. Accordingly, the influence of the RANKL peptide on osteoclasts was examined. The specific examination procedures were as follows. MHP1 (final concentration: 100 µg/ml) or RANKL protein (final concentration: 10 ng/ml) was added to a medium (DMEM medium (+4% FBS)) in which RAW264.7 cells were cultured, and the cells were collected after 10 minutes and 3 days.

Figure 12:
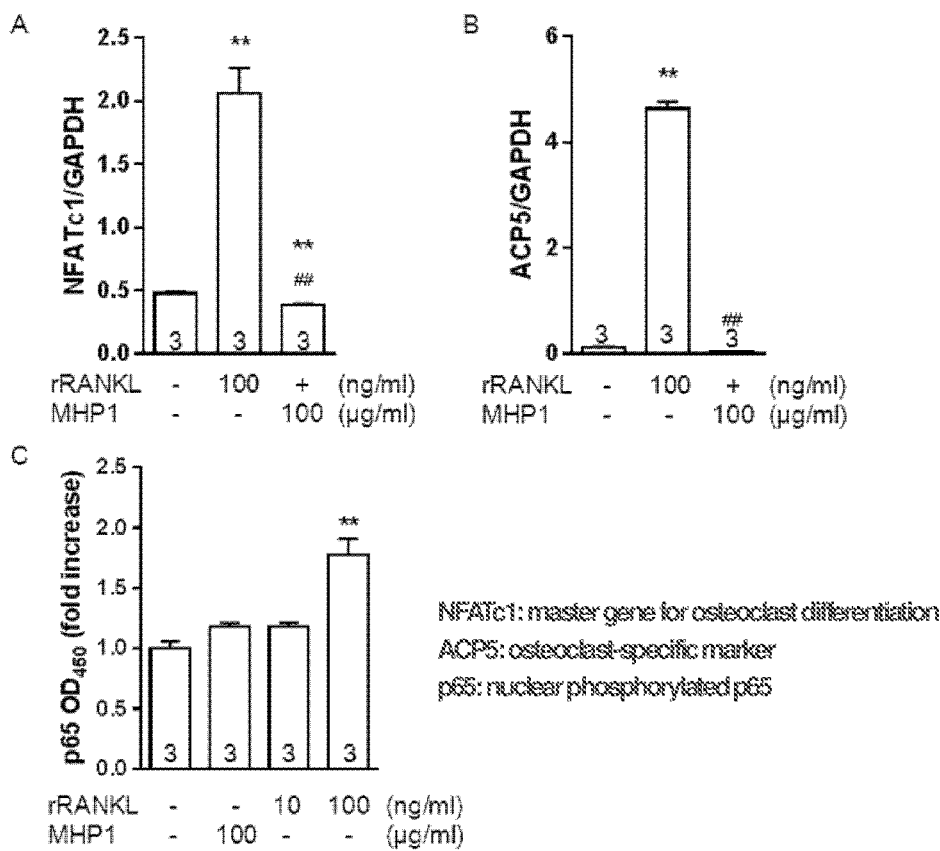
FIG. 12 shows the results of examining the influence of the RANKL peptide on osteoclasts (Example 7).

For the samples collected after 10 minutes, nuclear proteins of the cells were extracted using the Nuclear Extract Kit (Active Motif), and the degree of NFκB (p65) activation was measured by the TransAM NFκB p65 Kit (Active Motif). On the other hand, for the samples collected after 3 days, the mRNA expression levels of NFATc1 and ACP5 were analyzed by real-time RT-PCR. FIG. 12 shows the results.

FIG. 12 revealed that MHP1 slightly activated NFκB, but did not promote the expression of osteoclast-related mRNA.

Example 8: Analysis 2 of Influence of RANKL Peptide on Osteoclasts

Figure 13:
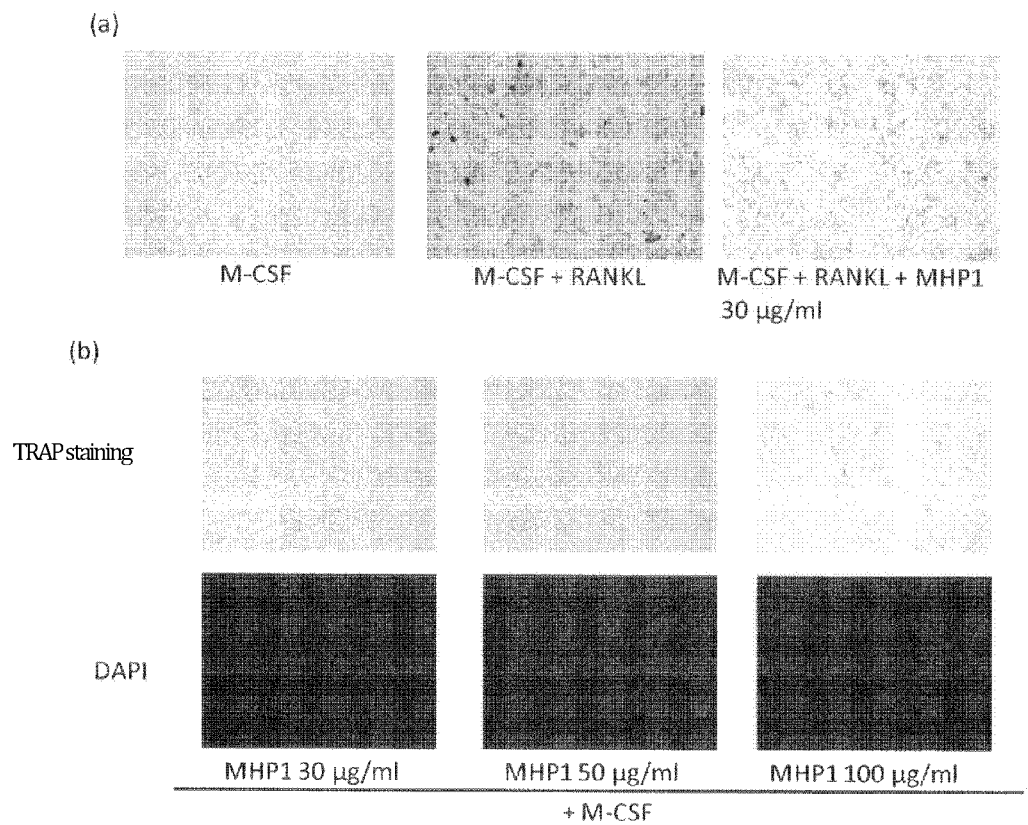
FIG. 13 shows the results of examining the influence of the RANKL peptide on osteoclasts (Example 8). (a) shows TRAP staining images of the A, B, and D groups, and (b) shows TRAP staining images (upper row) and nuclear staining images (lower row) of the C group.

Osteoclast Culture Kit V-2 (OSC33, produced by Cosmo Bio Co., Ltd.) was used. According to the manual of the kit, culture of osteoclast precursor cells was started in the presence of M-CSF (final concentration: 50 ng/ml) in the A and B groups, and in the presence of M-CSF (final concentration: 50 ng/ml) and MHP1 (final concentration: 30, 50, or 100 µg/ml) in the C and D groups. Thereafter, 24 hours to 7 days after the start of culture, the A group was cultured in the presence of M-CSF (final concentration: 50 ng/ml), the B group was cultured in the presence of M-CSF (final concentration: 50 ng/ml) and RANKL protein (final concentration: 50 ng/ml), the C group was cultured in the presence of M-CSF (final concentration: 50 ng/ml) and MHP1 (final concentration: 30, 50, or 100 µg/ml), and the D group was cultured in the presence of M-CSF (final concentration: 50 ng/ml), RANKL protein (final concentration: 50 ng/ml), and MHP1 (final concentration: 30, 50, or 100 µg/ml). After culture, the cells were subjected to TRAP staining and nuclear staining according to a standard method. FIG. 13 shows the results. FIG. 13 (a) shows TRAP staining images of the A, B, and D groups, and FIG. 13 (b) shows TRAP staining images and nuclear staining images of the C group.

FIG. 13 (a) indicated that the differentiation of osteoclasts promoted by RANKL was inhibited by MHP1 (comparison between the B group and the C group). FIG. 13 (b) indicated that the differentiation of osteoclasts did not occur even when MHP1 was added.

Example 9: Proinflammatory Cytokine Secretion Inhibition by RANKL Peptide (Human Macrophage Cells)

An examination was conducted into whether proinflammatory cytokine secretion inhibition by the RANKL peptide (Example 2, etc.) occurred in human cells. The specific examination procedures were as follows.

Figure 14:
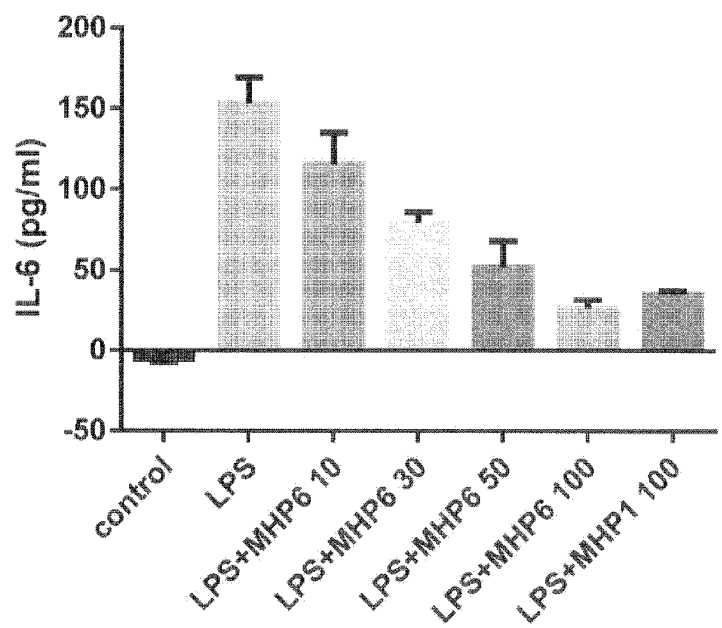
FIG. 14 shows the results of examining whether proinflammatory cytokine secretion inhibition by the RANKL peptide occurs in human cells (Example 9). The vertical axis represents the IL-6 concentration of the medium measured by ELISA. In the horizontal axis, the first column (control) from the left shows a case in which neither LPS nor RANKL peptide was contained in the medium, the second column (LPS) shows a case in which only LPS was contained in the medium, and the third to seventh columns show a case in which LPS and RANKL peptide (the final concentration (μg/ml) is described in each column) were both contained in the medium.

THP1 cells (human-derived macrophage cell line) were cultured in a DMEM medium (+4% FBS) containing MHP6 (human-derived; final concentration: 10, 30, 50, or 100 µg/ml) or MHP1 (mouse-derived; final concentration: 100 µg/ml), and LPS (final concentration: 2 ng/ml) for 24 hours by a standard method. After culture, the concentration of IL-6 in the medium was measured by the ELISA method. FIG. 14 shows the results.

FIG. 14 revealed that human-derived MHP6 and mouse-derived MHP1 both exhibited proinflammatory cytokine secretion-inhibiting activity on the human-derived macrophage cells.

Example 10: Necrosis Inhibition by RANKL Peptide

The influence of the RANKL peptide on the size of necrotic area after cerebral ischemia was examined. The specific examination procedures were as follows.

Figure 15:
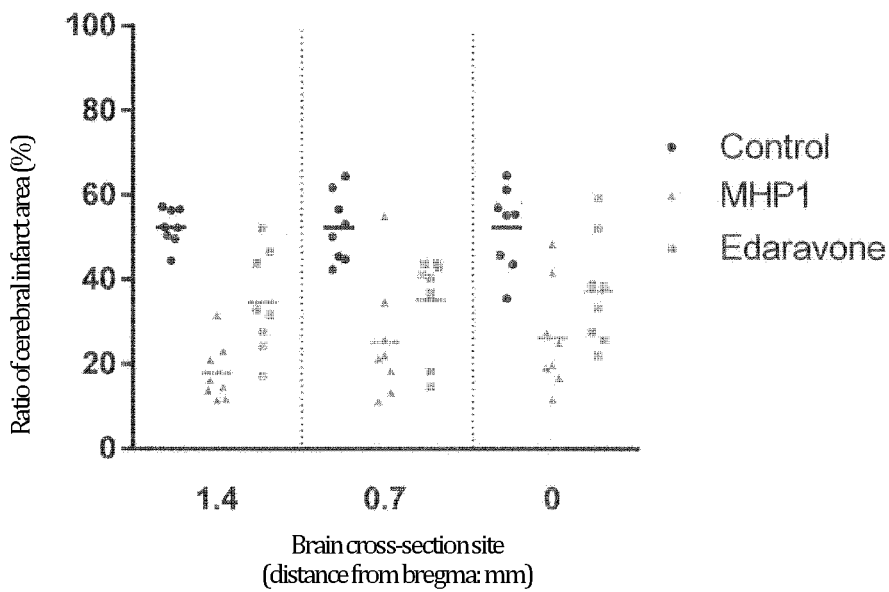
FIG. 15 shows the results of examining the influence of the RANKL peptide on the size of necrotic area after cerebral ischemia (Example 10). The vertical axis represents the ratio of the measured cerebral infarct area. The horizontal axis represents the brain cross-section site of the measurement object. Each plot shows the measurement results of each mouse, and each bar shows the average value. "Control" represents an aCSF administration group, "MHP1" represents an MHP1 solution administration group, and "Edaravone" represents an edaravone administration group.

A cerebral ischemic area was artificially developed in wild-type mice (C57BL6/J) using embolic suture. Specifically, nylon suture was inserted from the right external carotid artery into the intracranial internal carotid artery, and the right middle cerebral artery was temporarily occluded. The embolic suture was removed 40 minutes after the formation of the ischemic area, and the blood was reperfused. Four hours after the formation of the ischemic area, 2 µl of MHP1 solution (0.625 µg/2 µl, the solvent was artificial cerebrospinal fluid (aCSF)) or 2 µl of aCSF was administered by injection into the ventricle of the mice with a neurological severe score of 1 or 2. Separately, a group to which edaravone, which is a known brain-protecting agent, was administered was also produced (aCSF intraventricular administration+3 mg/kg of edaravone i.p., administered every 12 hours). The brain was removed 72 hours after the formation of the ischemic area, and a brain slice including left and right brain portions in positions of 1.4, 0.7, and 0 mm in the front and rear of the bregma was produced. The slice was stained with cresyl violet. The area of the cresyl violet staining site was regarded as the cerebral infarct area (necrosis site), and the ratio of cerebral infarct area was determined by the following formula. FIG. 15 shows the results.

Ratio of cerebral infarct area=([normal side brain area]−([cerebral infarct side total area]−[cerebral infarct area])/normal side brain area)×100

Figure 16:
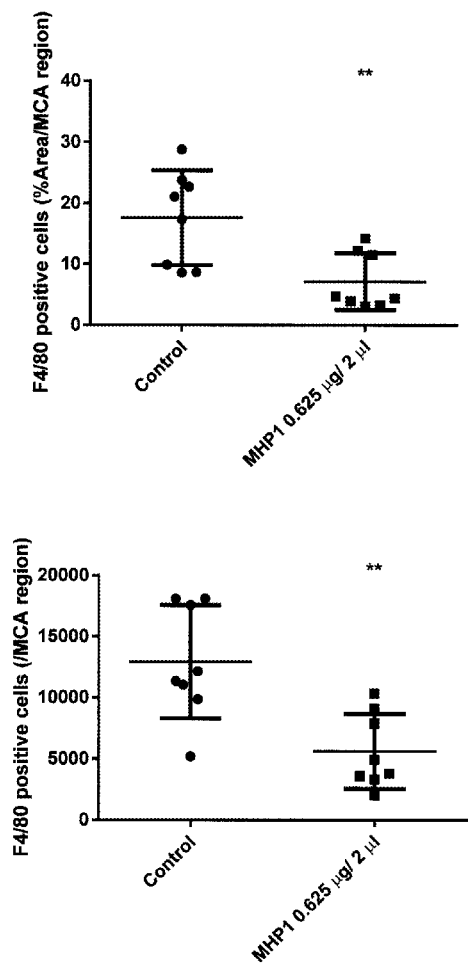
FIG. 16 shows the ratio of F4/80-positive cells (activated macrophage/microglia) in the cerebral infarction hemisphere (/middle cerebral artery region), and the results of measuring the number of the cells (Example 10). Each plot shows the measurement results of each mouse, the middle bar shows the average value, and the upper-end bar and the lower-end bar show standard deviation. "**" indicates that the P-value relative to control was less than 0.01.

FIG. 15 revealed that necrosis occurring after cerebral ischemia could be inhibited by MHP1 (comparison between the control group and the MHP1 group). It was also indicated that in spite of one administration, the degree of inhibition of necrosis was higher than edaravone administration (comparison between the MHP1 group and the Edaravone group). Furthermore, the ratio of F4/80-positive cells (activated macrophage/microglia) in the cerebral infarction hemisphere in a position of 0.7 mm from the bregma (/middle cerebral artery region), and the number of the cells were measured. FIG. 16 shows the results. FIG. 16 (a) shows the measurement results of the ratio of F4/80-positive cells (activated macrophage/microglia) in the cerebral infarction hemisphere (/middle cerebral artery region), and FIG. 16 (b) shows the measurement results of the number of the cells.

FIG. 16 revealed that the expression of activated macrophage/microglia was suppressed by MHP1.

Example 11: Septicemia Preventive or Therapeutic Effects of RANKL Peptide

The septicemia preventive/therapeutic effects of the RANKL peptide were examined. The specific examination procedures were as follows.

Figure 17:
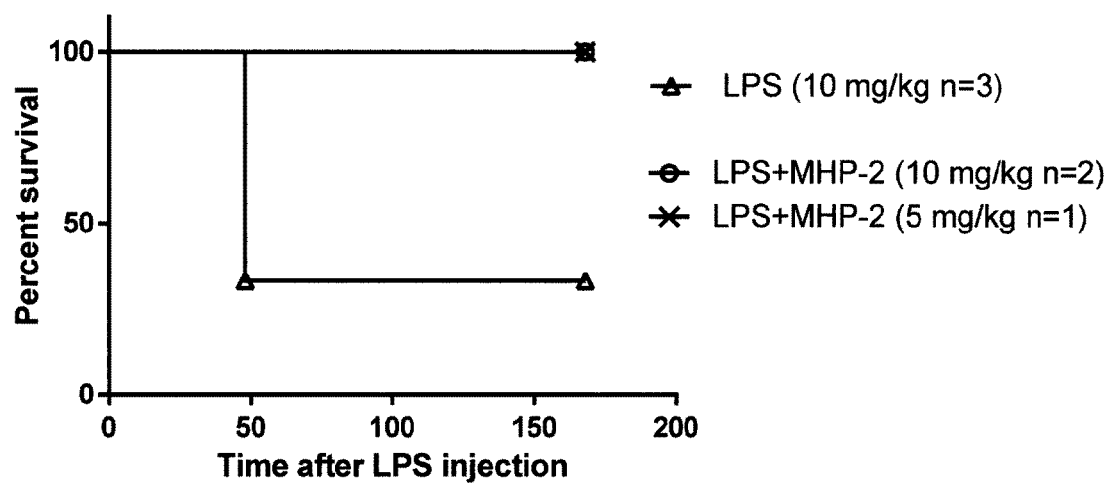
FIG. 17 shows the results of examining the septicemia preventive/therapeutic effects of the RANKL peptide (Example 11). The vertical axis represents the survival rate, and the horizontal axis represents the number of days after LPS administration.

To wild-type mice (Balb/c, 5-week-old female mice), LPS (10 mg/kg) was intraperitoneally administered, or LPS (10 mg/kg) and MHP-2 (5 mg/kg or 10 mg/kg) were intraperitoneally administered. After administration, the survival rate of the mice was measured. FIG. 17 shows the results.

FIG. 17 indicated that 2 of 3 mice in the group to which only LPS was administered (Δ) died, whereas no mouse in the groups to which LPS and MHP2 were administered (○ and x) died. This revealed that the RANKL peptide had preventive/therapeutic effects on septicemia.

Example 12: Stability of RANKL Peptide

The stability of the RANKL peptide was examined. The specific examination procedures were as follows.

Figure 18:
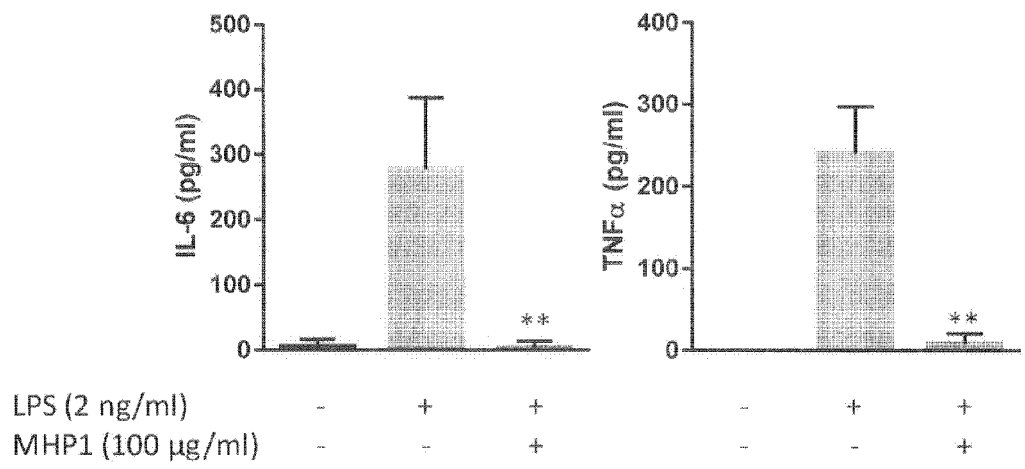
FIG. 18 shows the results of examining the stability of the RANKL peptide (Example 12). The vertical axis represents the concentration of IL-6 or TNF-α in the medium measured by ELISA. "**" indicates that the P-value relative to control was less than 0.01.

MHP1 was dissolved in water to a concentration of 2 mg/ml, and stored at 4° C. for 208 days. Thereafter, the proinflammatory cytokine secretion-inhibiting effect of this MHP1 was examined in the same manner as in Example 2, except that the final concentration of MHP1 was set to 100 μg/ml. FIG. 18 shows the results.

FIG. 18 revealed that MHP1 exhibited a proinflammatory cytokine secretion-inhibiting effect even after long-term storage, in the same manner as MHP1 before storage. This indicated that the stability of MHP1 was high.

Example 13: Comparison Between RANKL Peptide and RANKL Full-Length Protein

Figure 19:
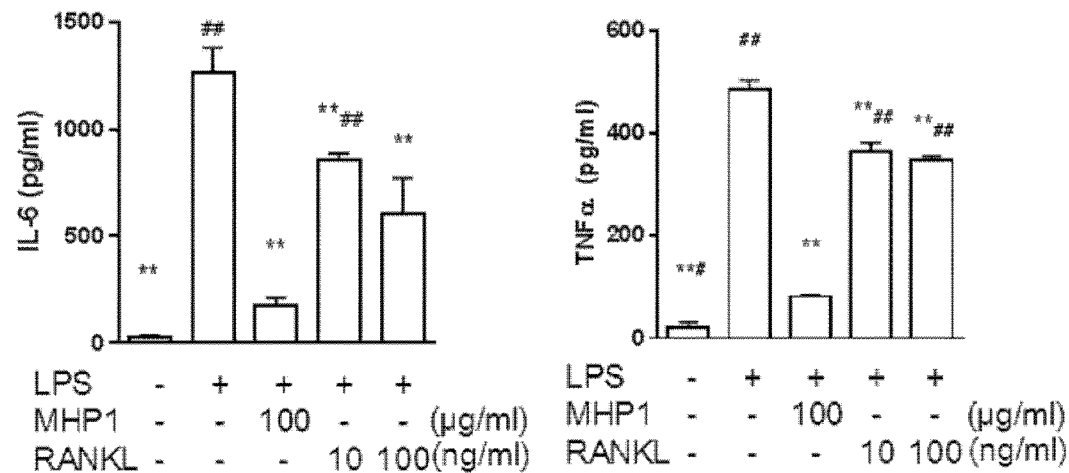
FIG. 19 shows the results of the comparison between the RANKL peptide and RANKL full-length protein (Example 13). The vertical axis represents the concentration of IL-6 or TNF-α in the medium measured by ELISA. "**" indicates that the P-value relative to control was less than 0.01.

The proinflammatory cytokine secretion-inhibiting effect was examined in the same as in Example 2, except that the final concentration of MHP1 was set to 100 μg/ml, and that RANKL full-length protein was used at a final concentration of 10 ng/ml or 100 ng/ml as the comparison target. The final concentration of RANKL full-length protein was a concentration in which its effect was efficiently exhibited, and the concentration was determined based on known documents (J Immunol 177 (6): 3799-3805, and Shimamura M, et al. (2014) "OPG/RANKL/RANK axis is a critical inflammatory signaling system in ischemic brain in mice," Proc Natl Acad Sci USA, 111 (22): 8191-8196). FIG. 19 shows the results.

FIG. 19 revealed that the RANKL peptide of the present invention had a proinflammatory cytokine secretion-inhibiting effect higher than that of RANKL full-length protein.

Example 14: Effect of RANKL Peptide on Proinflammatory Cytokine Secretion by TLR2

Figure 20:
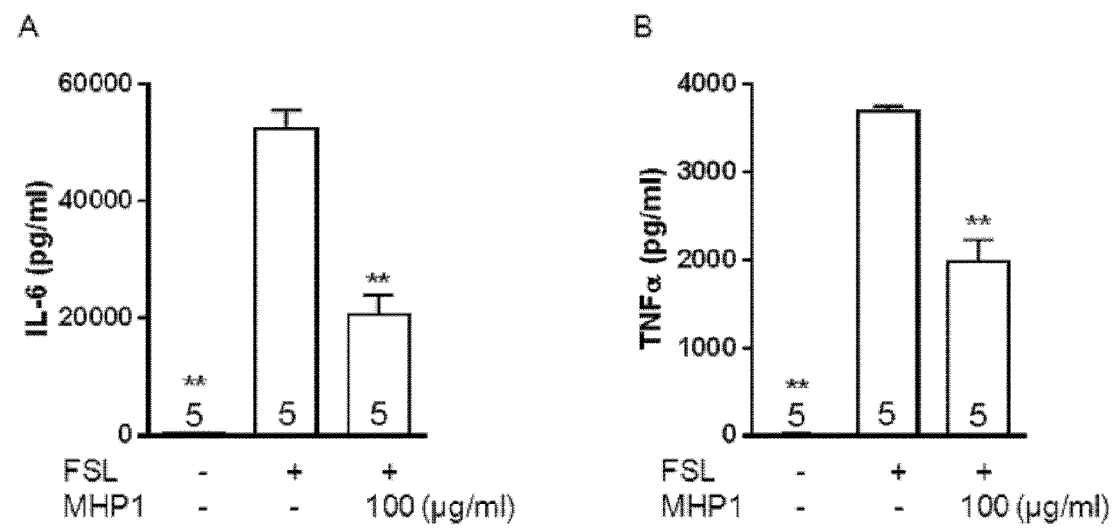
FIG. 20 shows the test results regarding the effects of the RANKL peptide on proinflammatory cytokine secretion by TLR2 (Example 14). The vertical axis represents the concentration of IL-6 or TNF-α in the medium measured by ELISA. "**" indicates that the P-value relative to control was less than 0.01.

The proinflammatory cytokine secretion-inhibiting effect was examined in the same manner as in Example 2, except that FSL-1, which is a TLR2/6 ligand, was used in place of LPS. FIG. 20 shows the results.

FIG. 20 revealed that the RANKL peptide of the present invention also had a proinflammatory cytokine secretion-inhibiting effect on proinflammatory cytokine secretion by TLR2.

Example 15: Kinetic Analysis after Intravenous Administration of RANKL Peptide

Figure 21:
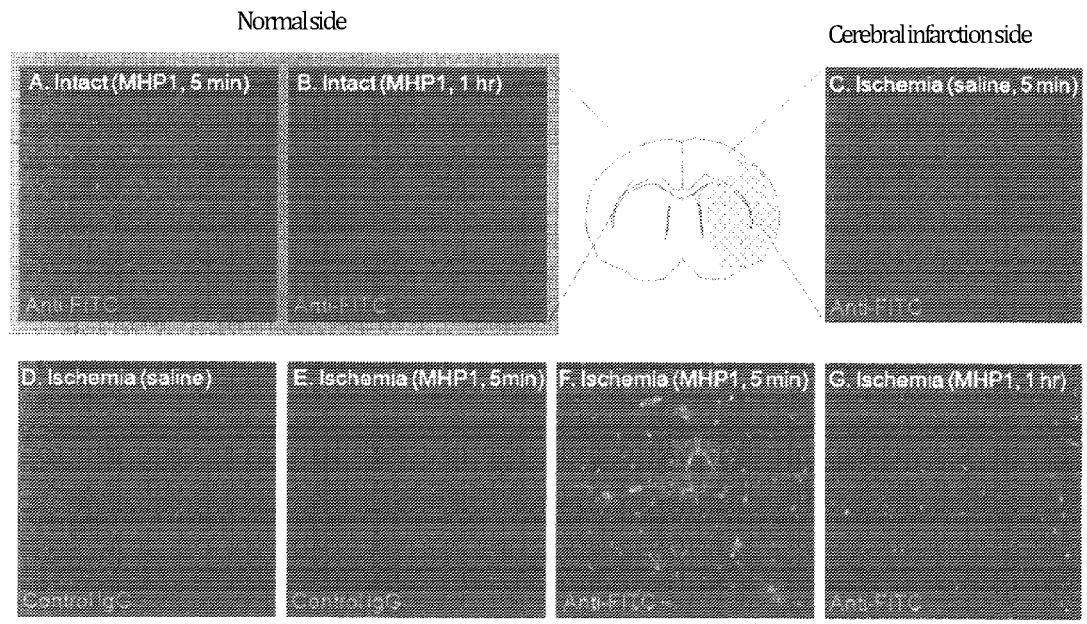
FIG. 21 shows the results of kinetic analysis after intravenous administration of the RANKL peptide (Example 15). In the photographs, "Intact" shows photographs of tissue on the side in which a cerebral infarction model was not produced, "Ischemia" shows photographs of tissue on the side in which a cerebral infarction model was produced, "5 min" and "1 hr" represent the time elapsed after administration, and "saline" represents a case of administering physiological saline in place of an administration solution.

Cerebral infarction models were produced in the same manner as in Example 10. Separately, 200 μg of MHP1 labeled with FITC was dissolved in 200 μl of physiological saline to obtain an administration solution. The administration solution was intravenously injected through the cervical vein 4 hours after the production of the cerebral infarct models. The mice were sacrificed 5 minutes and 1 hour after administration, and brain tissue was produced by a standard method. The brain tissue was immunostained with anti-FITC antibody (Abcam), and observed with a confocal microscope. FIG. 21 shows the results.

FIG. 21 revealed that the RANKL peptide of the present invention infiltrated into the brain parenchyma after intravenous administration.

Example 16: Necrosis Inhibition by Intravenous Administration of RANKL Peptide

Figure 22:
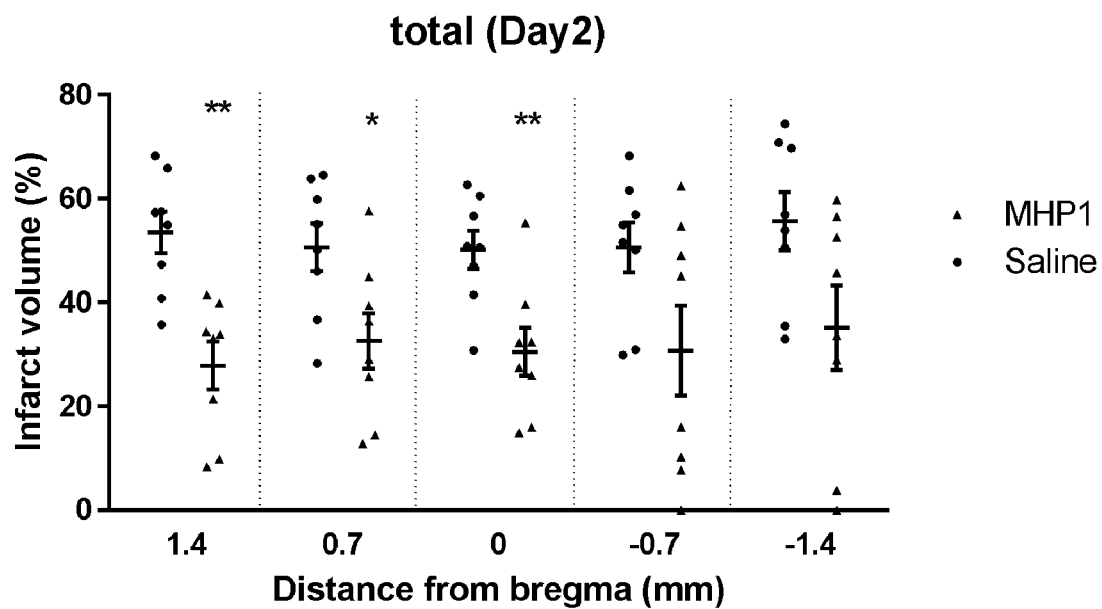
FIG. 22 shows the results of examining the influence of the RANKL peptide on the size of necrotic area after cerebral ischemia (Example 16). The vertical axis represents the ratio of the measured cerebral infarct area. The horizontal axis represents the brain cross-section site of the measurement object. Each plot shows the measurement results of each mouse, and each bar shows the average value. "Saline" represents a physiological saline administration group, and "MHP1" represents an MHP1 administration solution administration group.

Cerebral infarction models were produced in the same manner as in Example 10. Four hours after the production of the cerebral infarct models, 300 μG/150 μL of MHP1 administration solution was administered through the cervical vein to the mice with a neurological severity score of 1 or 2. Thereafter, 336 μg was continuously administered by subcutaneous injection using an Alzet pump for 21 hours. Twenty-four hours and forty-eight hours after the production of the cerebral infarction models, neurological severity scores were measured. Furthermore, the mice were sacrificed 48 hours after the production of the cerebral infarction models, and the ratio of cerebral infarct area was determined in the same manner as in Example 10. FIG. 22 shows the ratio of cerebral infarct area, and FIG. 23 shows neurological severity scores.

Figure 23:
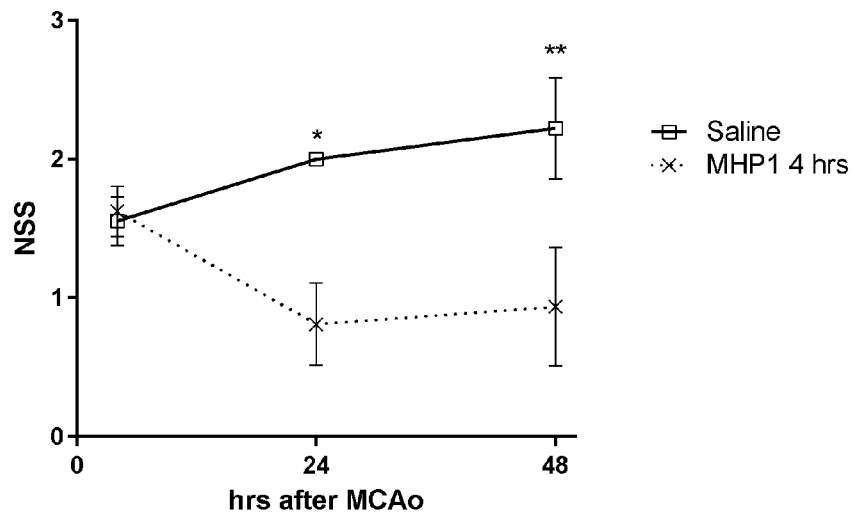
FIG. 23 shows the results of examining the influence of the RANKL peptide on cerebral infarction symptoms after cerebral ischemia (Example 16). The vertical axis represents the measured neurological severity scores, and the horizontal axis represents the time elapsed after the production of cerebral infarction models. "Saline" represents a physiological saline administration group, and "MHP1" represents an MHP1 administration solution administration group.

FIGS. 22 and 23 revealed that necrosis occurring after cerebral ischemia could be suppressed by the intravenous administration of MHP1, and that the symptoms of cerebral infarction could be relieved.

Example 17: Analysis 3 of Influence of RANKL Peptide on Osteoclasts

Figure 24:
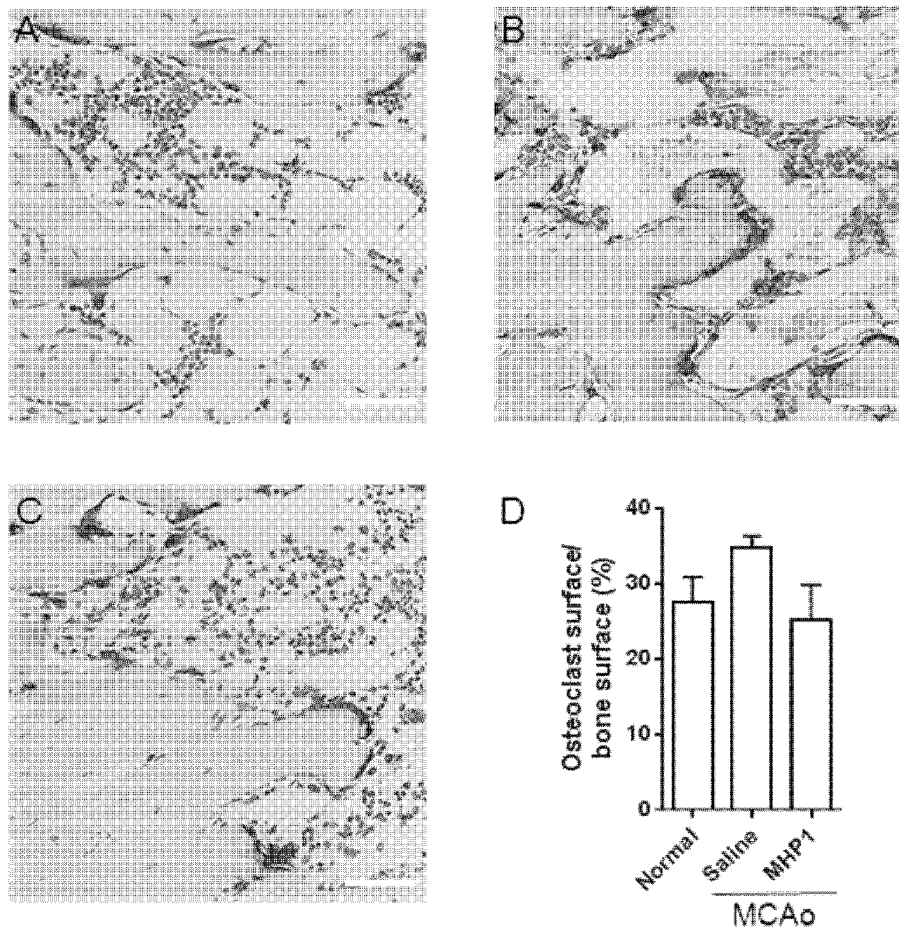
FIG. 24 shows the results of examining the influence of RANKL peptide administration on osteoclasts (Example 17). A to C show TRAP staining images. A: normal mouse, B: cerebral infarction mouse (physiological saline administration), and C: cerebral infarction mouse (MHP1 administration). The vertical axis of D represents the ratio of the stained region (osteoclast surface) relative to the bone surface in the TRAP staining images. In the horizontal axis of D, "Normal" represents a normal mouse group (A), "Saline" represents a group (B) to which physiological saline was administered after cerebral infarction, and "MHP1" represents a group (C) to which an MHP1 administration solution was administered after cerebral infarction.

Cerebral infarction models were produced in the same manner as in Example 10. Four hours after the production of the cerebral infarction models, 300 μG/150 μL of MHP1 administration solution was administered through the cervical vein. Thereafter, 336 μg was continuously administered by subcutaneous injection using an Alzet pump for 21 hours. Forty-eight hours after the production of the cerebral infarction models, the radius distal portion of the left hand (paralyzed side) was stained with TRAP, and the ratio of the stained region (osteoclast surface) relative to the bone surface was calculated based on the obtained staining images. FIG. 24 shows the results.

As shown in FIG. 24, the number of TRAP-positive osteoclasts (red cells) on the bone ridge increased due to cerebral infarction; however, the increase was suppressed in the MHP1 administration mouse.

Figure 25:
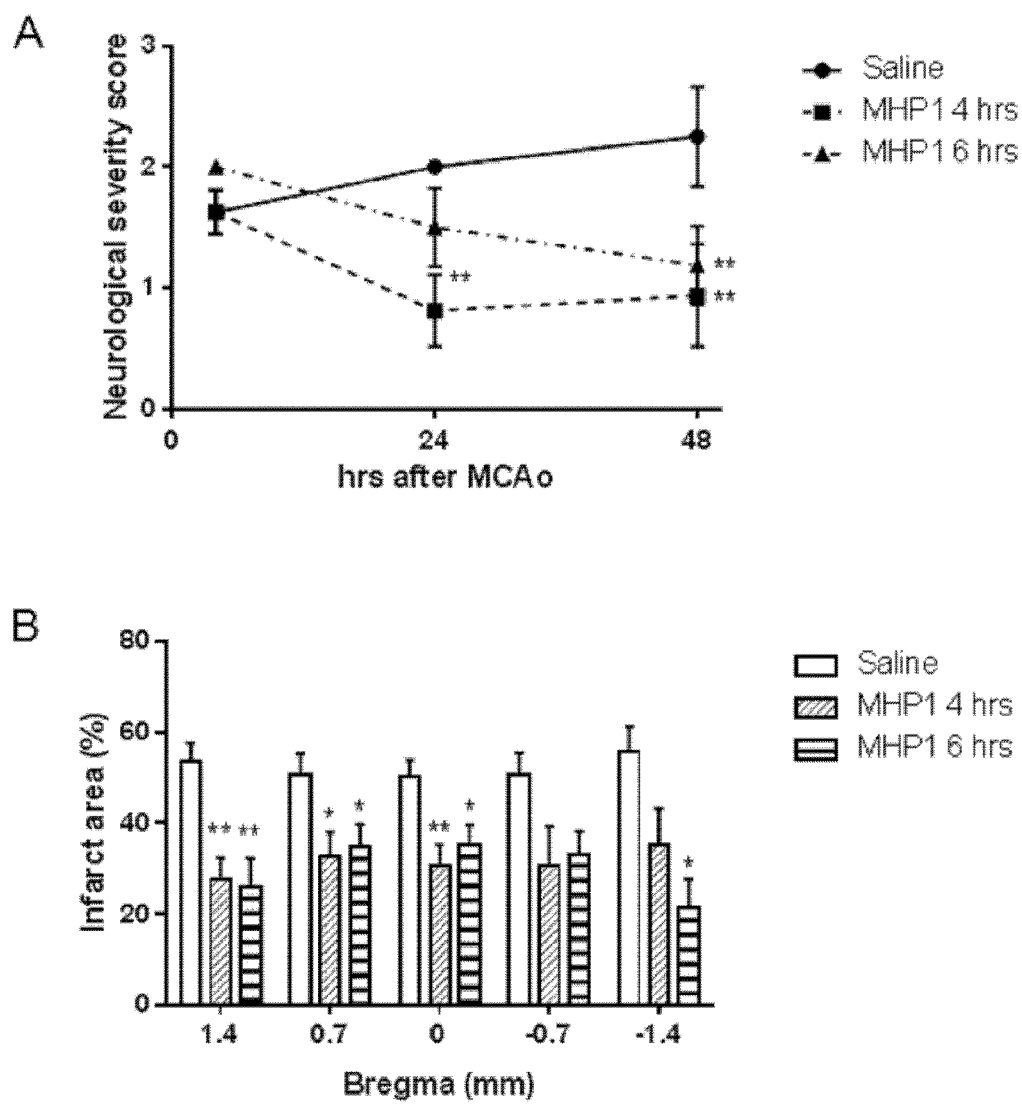
FIG. 25 shows the results of examining the effects of RANKL peptide administration 6 hours after cerebral infarction (Example 18). In A, the vertical axis represents the measured neurological severity scores, and the horizontal axis represents the time elapsed after the production of cerebral infarction models. In B, the vertical axis represents the ratio of the measured cerebral infarct area, and the horizontal axis represents the brain cross-section site of the measurement object. In B, each plot shows the measurement results of each mouse, and each bar shows the average value. In A and B, "Saline" represents a physiological saline administration group, and "MHP1 4 (or 6) hrs" represents a group to which an MHP1 administration solution was administered 4 (or 6) hours after the production of cerebral infarction models.

Example 18: Necrosis Inhibition by RANKL Peptide Administration 6 Hours after Cerebral Infarction A test was performed in the same manner as in Example 16, except that the administration of MHP1 was started 4 hours or 6 hours after the production of cerebral infarction models. FIG. 25 shows neurological severity scores and the ratio of cerebral infarct area.

SEQUENCE LISTING

The invention claimed is:

1. An oligopeptide having inhibitory activity on proinflammatory cytokine secretion from cells, the oligopeptide containing a DE loop sequence of RANKL protein, a β-strand D sequence of RANKL protein adjacent to the N-terminal side of the DE loop sequence, and a β-strand E sequence of RANKL protein adjacent to the C-terminal side of the DE loop sequence, wherein the oligopeptide is free of a CD loop sequence of RANKL protein, the DE loop sequence has the amino acid sequence of SEQ ID NO: 1, the β-strand D sequence has the amino acid sequence of any one of SEQ ID NOs: 2 to 5, the β-strand E sequence has the amino acid sequence of any one of SEQ ID NOs: 6 to 9, and the length of the oligopeptide is no more than 50 amino acid residues.

2. The oligopeptide according to claim 1, wherein the oligopeptide consists of the amino acid sequence of any one of SEQ ID NOs: 10, 11, 13, 14, 22, and 23, or the amino acid sequence of any one of SEQ ID NOs: 10, 11, 13, 14, 22, and 23 having one or two amino acid substitutions, deletions, additions, or insertions.

3. The oligopeptide according to claim 2, wherein the amino acid sequence of any one of SEQ ID NOs: 10, 11, 13, 14, 22, and 23 has one amino acid substituted, deleted, added, or inserted.

4. The oligopeptide according to claim 2, wherein the oligopeptide consists of the amino acid sequence of any one of SEQ ID NOs: 10, 11, 13, 14, 22, and 23.

5. A pharmaceutical preparation comprising the oligopeptide according to claim 1.

6. A method for treating a disease selected from the group consisting of cerebral infarction and septicemia, the method comprising administering the oligopeptide according to claim 1 to a patient in need thereof.

7. The method according to claim 6, wherein the disease is cerebral infarction.

8. A pharmaceutical preparation for preventing or treating an infarction disease, the pharmaceutical preparation comprising the oligopeptide according to claim 1.

* * * * *